US011478486B2

(12) United States Patent
Gongora et al.

(10) Patent No.: US 11,478,486 B2
(45) Date of Patent: Oct. 25, 2022

(54) ASSOCIATION OF ACTIVES FOR TREATING PROSTATE CANCER

(71) Applicants: INSTITUT RÉGIONAL DU CANCER DE MONTPELLIER (ICM), Montpellier (FR); INSTITUT NATIONAL DE LA SANTÉ ET DE LA RECHERCHE MÉDICALE (INSERM), Paris (FR); UNIVERSITÉ DE MONTPELLIER, Montpellier (FR)

(72) Inventors: Céline Gongora, Montpellier (FR); Diego Tosi, Montpellier (FR)

(73) Assignees: INSTITUT REGIONAL DU CANCER DE MONTPELLIER (ICM), Montpellier (FR); INSTITUT NATIONAL DE LA SANTE ET DE LA RECHERCHE MEDICALE (INSERM), Paris (FR); UNIVERSITE DE MONTPELLIER, Montpellier (FR)

( * ) Notice: Subject to any disclaimer, the term of this patent is extended or adjusted under 35 U.S.C. 154(b) by 7 days.

(21) Appl. No.: 16/764,106

(22) PCT Filed: Nov. 14, 2018

(86) PCT No.: PCT/EP2018/081190
§ 371 (c)(1),
(2) Date: May 14, 2020

(87) PCT Pub. No.: WO2019/096824
PCT Pub. Date: May 23, 2019

(65) Prior Publication Data
US 2020/0390788 A1 Dec. 17, 2020

(30) Foreign Application Priority Data

Nov. 14, 2017 (EP) ..................... 17306576

(51) Int. Cl.
*A61K 31/4439* (2006.01)
*A61K 31/4166* (2006.01)
*A61K 31/58* (2006.01)
*A61P 35/00* (2006.01)
*A61K 9/00* (2006.01)
*A61K 31/4155* (2006.01)
*A61K 31/437* (2006.01)

(52) U.S. Cl.
CPC ............ *A61K 31/58* (2013.01); *A61K 9/0019* (2013.01); *A61K 9/0053* (2013.01); *A61K 31/4155* (2013.01); *A61K 31/4166* (2013.01); *A61K 31/437* (2013.01); *A61K 31/4439* (2013.01); *A61P 35/00* (2018.01)

(58) Field of Classification Search
CPC ............ A61K 31/4439; A61K 31/4166; A61K 31/44; A61P 35/00
USPC .................................................. 514/338, 386
See application file for complete search history.

(56) References Cited

U.S. PATENT DOCUMENTS

2015/0209359 A1    7/2015  Yaffe et al.

FOREIGN PATENT DOCUMENTS

WO    2015/065919 A1    5/2015
WO    2017/117182 A1    7/2017

OTHER PUBLICATIONS

Paranjape et al.: Inhibition of FOXC 2 restores epithelial phenotype and drug sensitivity in prostate cancer cells with stem-cell properties. Oncogene, vol. 35, pp. 5963-5976, 2016.*
Antonarakis et al: "AR-V7 and Resistance to Enzalutamide and Abiraterone in Prostate Cancer", New England Journal of Medicine, vol. 371, No. 11, pp. 1028-1038, Sep. 11, 2014.
Khandrika et al: "Hypoxia-associated p38 mitogen-activated protein kinase-mediated androgen receptor activation and increased HIF-1 [alpha] levels contribute to emergence of an aggressive phenotype in prostate cancer", Oncogene, vol. 28, No. 9, pp. 1248-1260, Jan. 19, 2009.

* cited by examiner

*Primary Examiner* — Charanjit Aulakh
(74) *Attorney, Agent, or Firm* — WCF IP

(57) ABSTRACT

The invention concerns a pharmaceutical combination of an inhibitor of the androgen receptor signaling pathway and of a p38 inhibitor for use in the treatment of prostate cancer in individuals wherein the prostate tumor cells express the AR-V7 variant androgen receptor protein or for preventing the occurrence of resistance in patients suffering from prostate cancer treated by an inhibitor of the androgen receptor signaling pathway. The invention further concerns a pharmaceutical composition comprising enzalutamide, abiraterone or apalutamide and a p38 inhibitor selected from LY2228820 and ARRY-614, and at least one pharmaceutically acceptable excipient. The invention also concerns the use of a p38 inhibitor for restoring the sensitivity to androgen-deprivation therapy (ADT) in patients suffering from prostate cancers having acquired a resistance to ADT following a treatment with an inhibitor of the androgen receptor signaling pathway and wherein the prostate tumour cells express the AR-V7 variant androgen receptor protein.

14 Claims, 24 Drawing Sheets

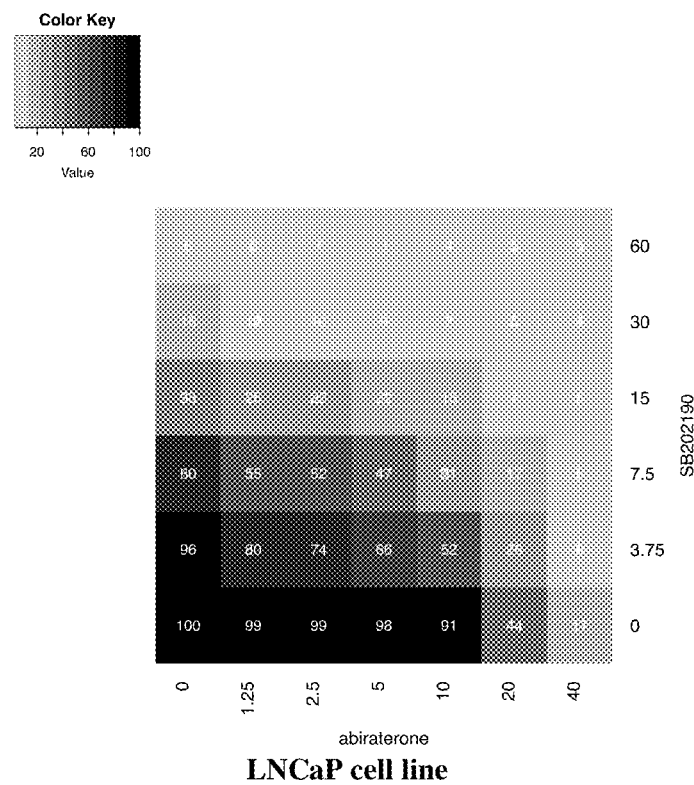
LNCaP cell line
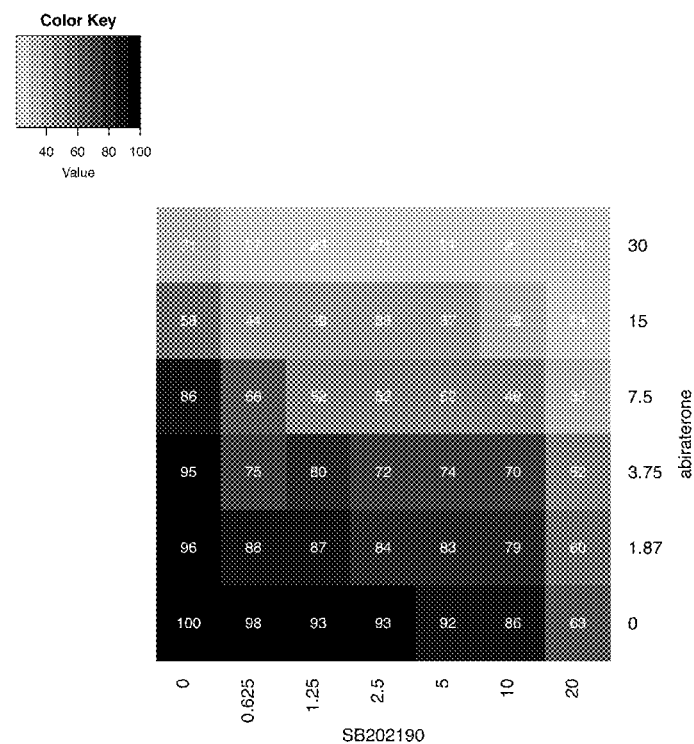
22Rv1 cell line
FIGURE 3A

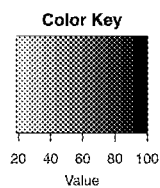
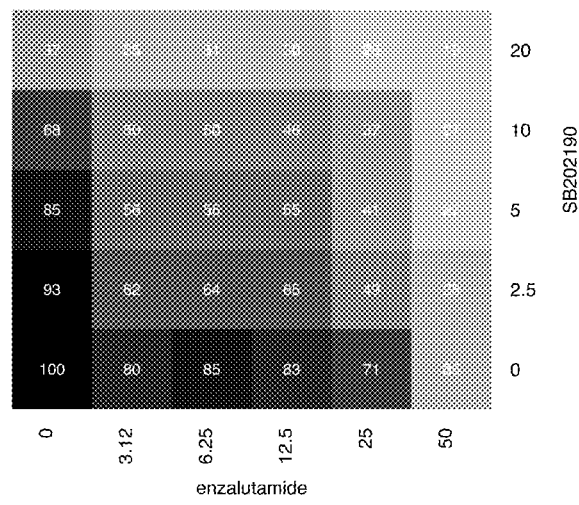
LNCaP cell line
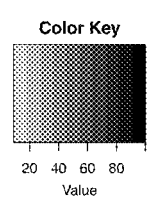
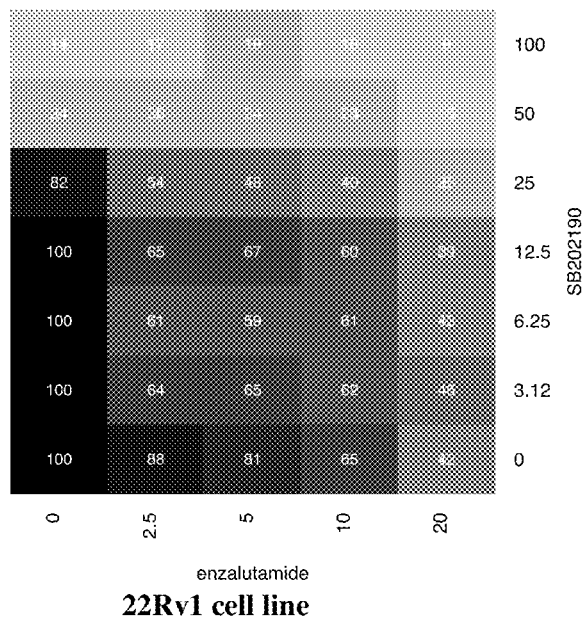
22Rv1 cell line
FIGURE 4A

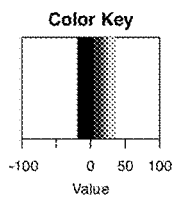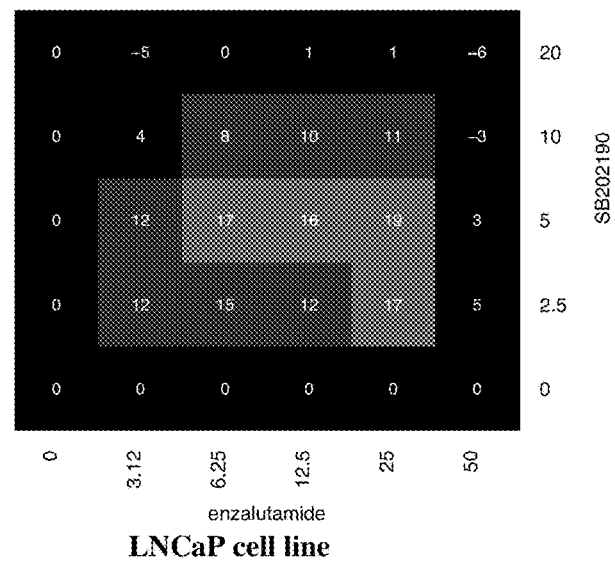
LNCaP cell line
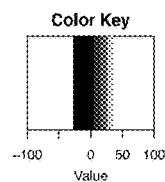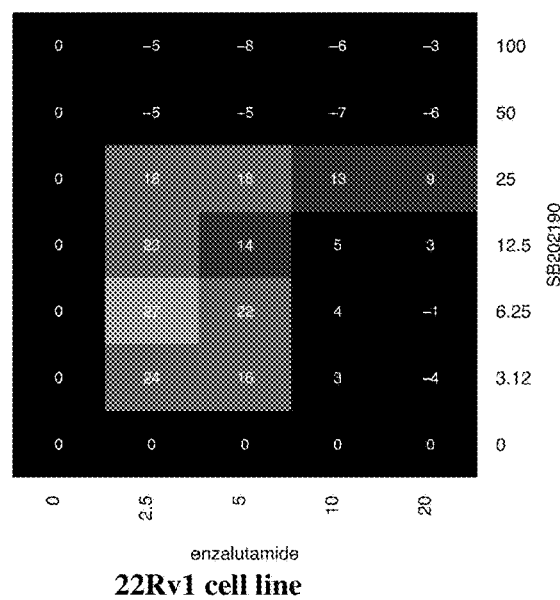
22Rv1 cell line
FIGURE 4B

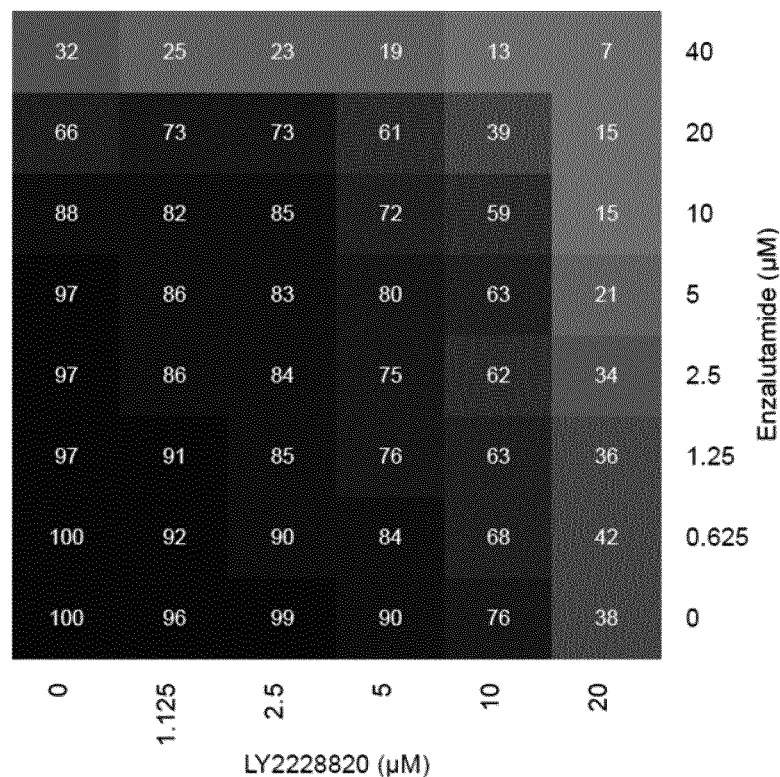
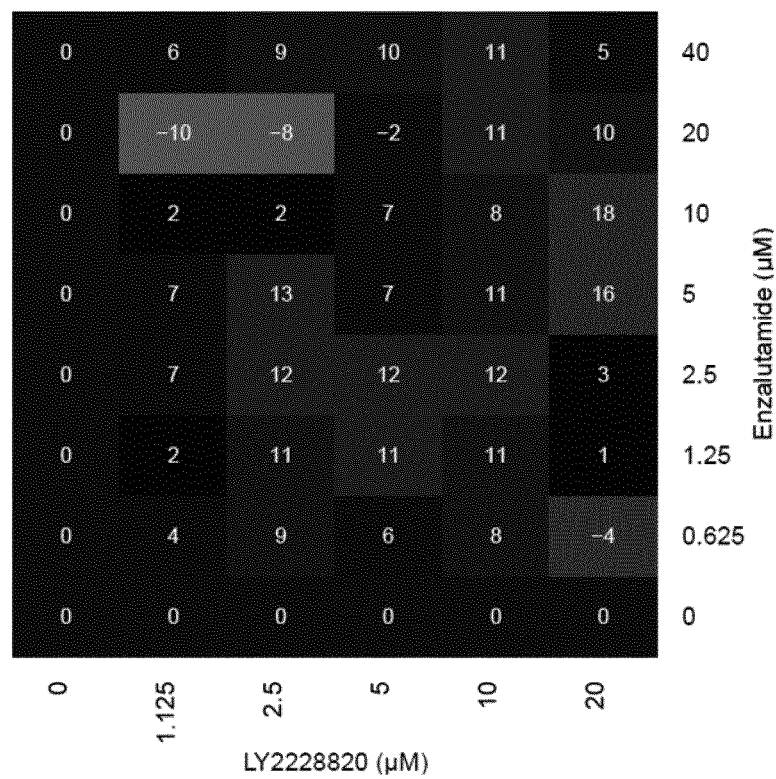
FIGURE 8A : 22Rv1 cell line

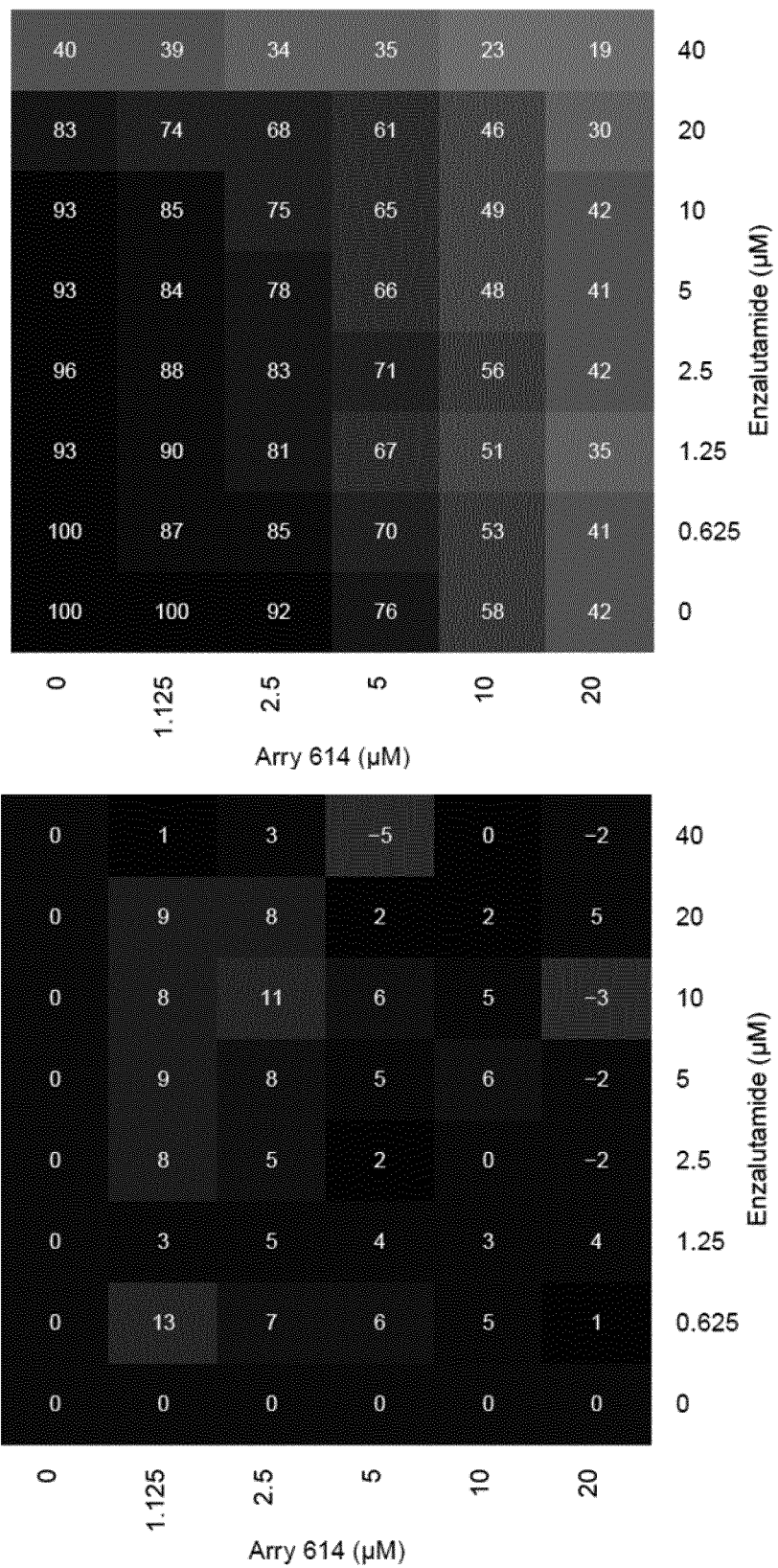
FIGURE 8B : 22Rv1 cell line

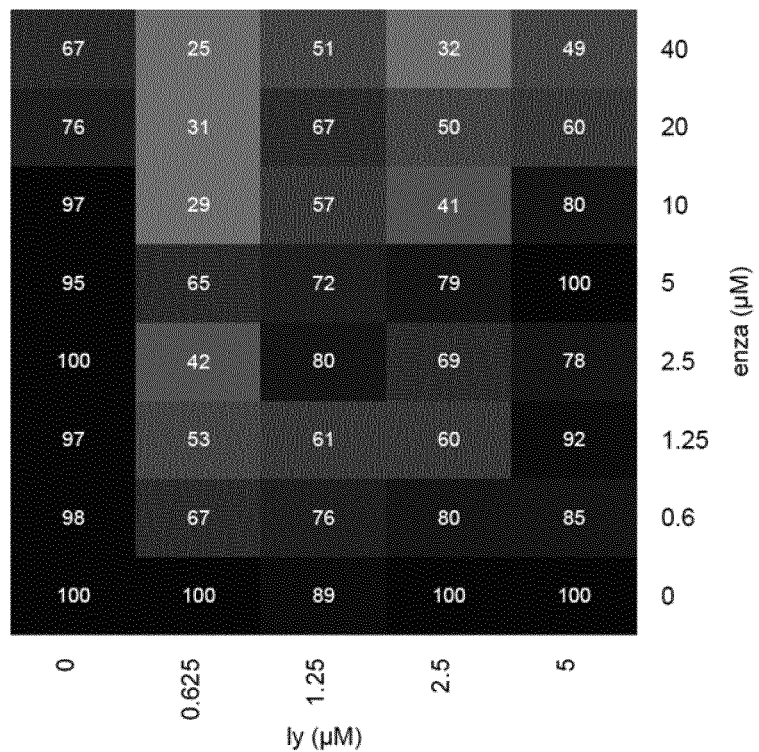
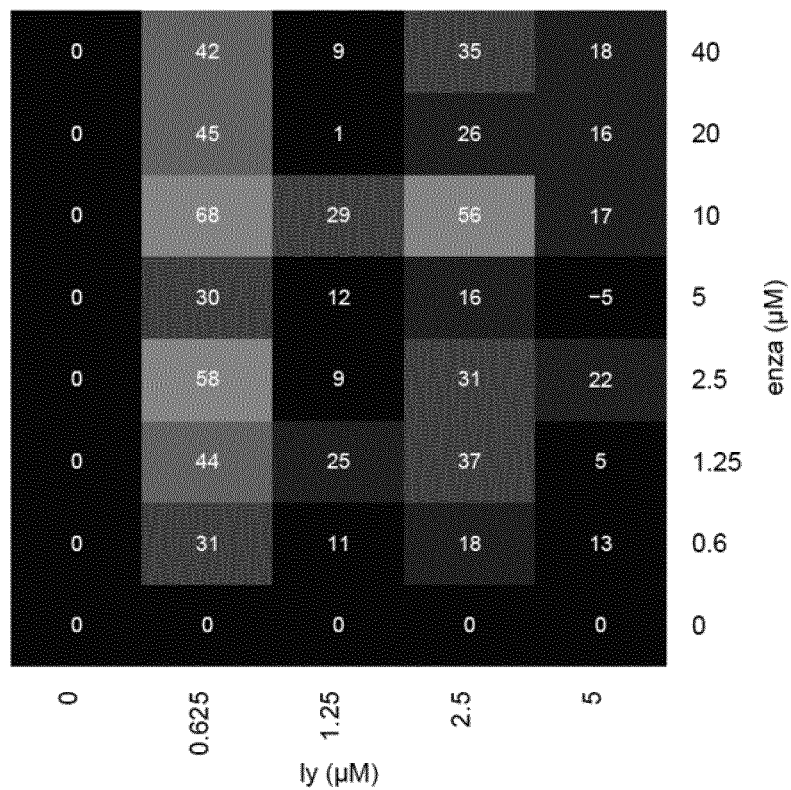
FIGURE 9A : 22Rv1 cell line

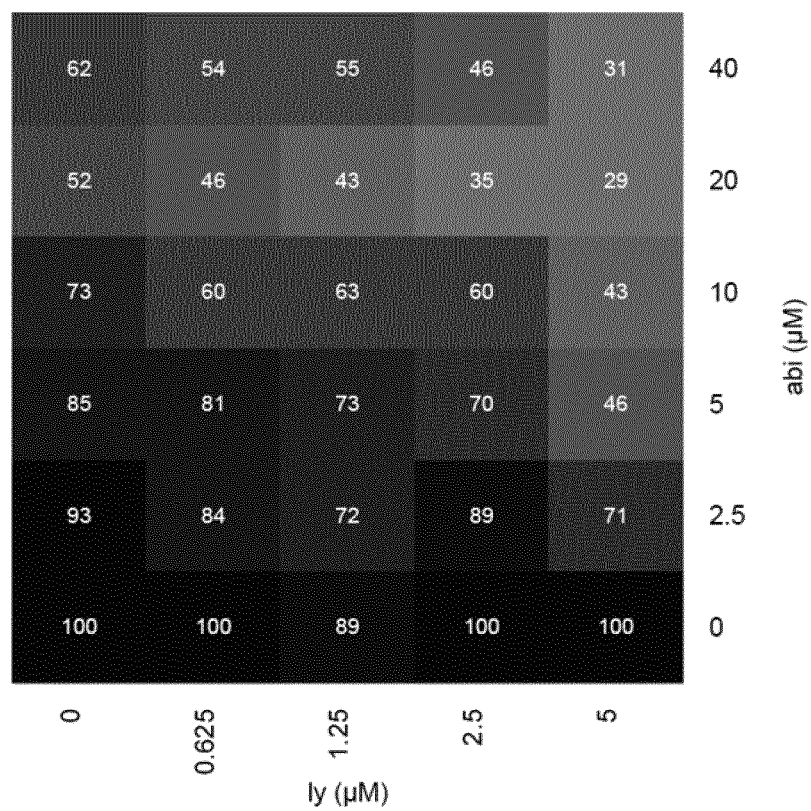
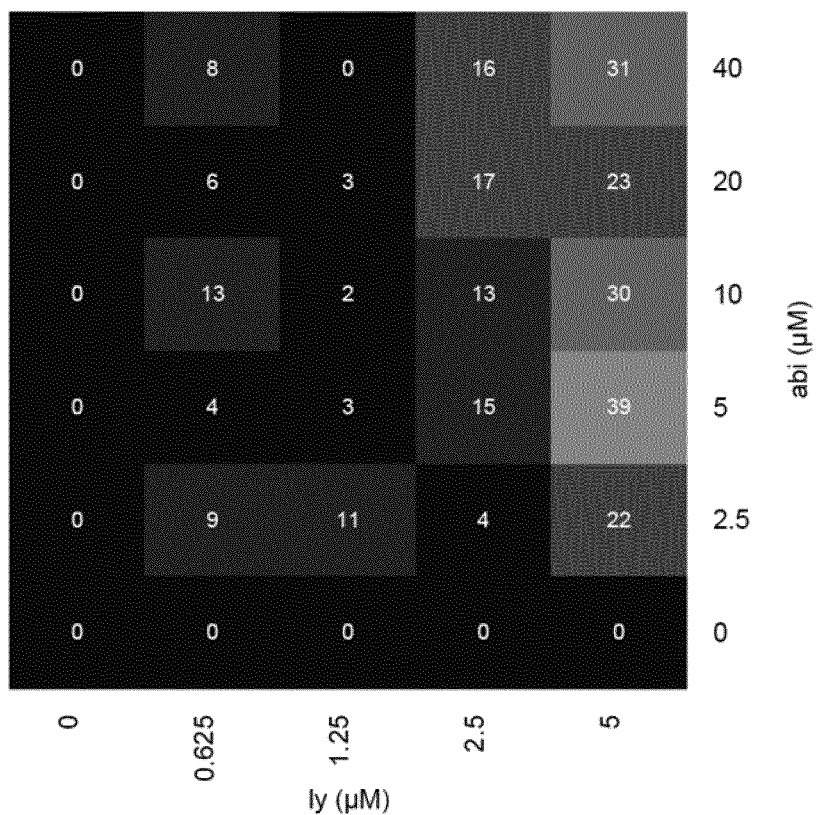
FIGURE 9B : 22Rv1 cell line

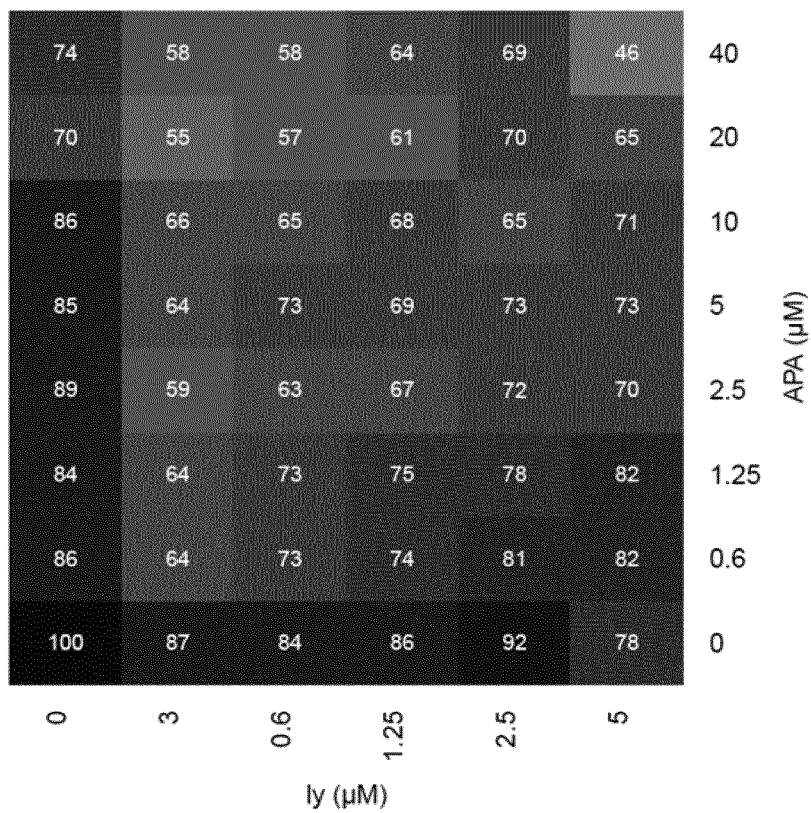
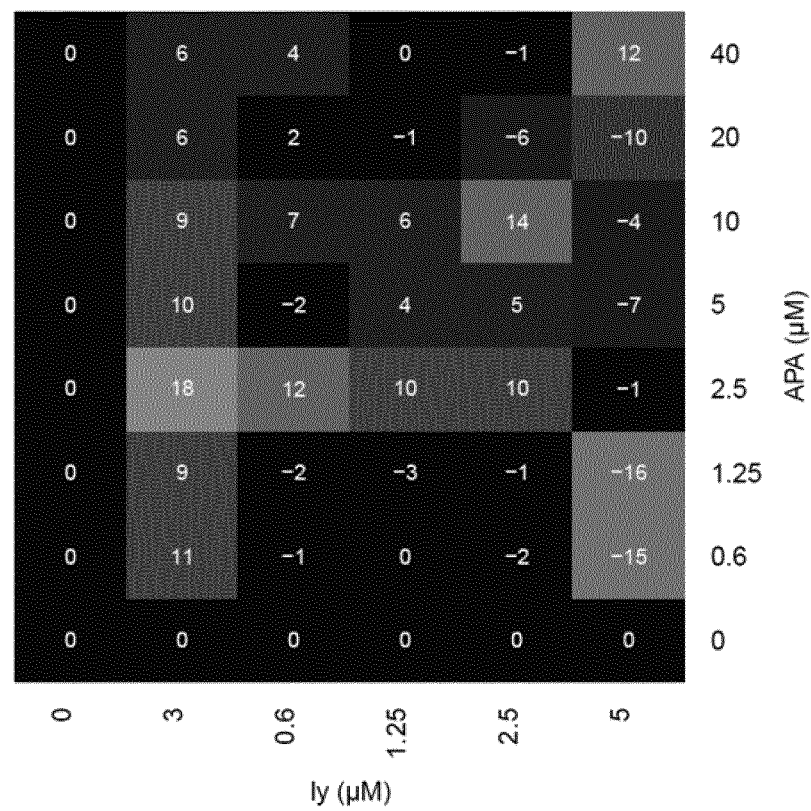
FIGURE 9C : 22Rv1 cell line

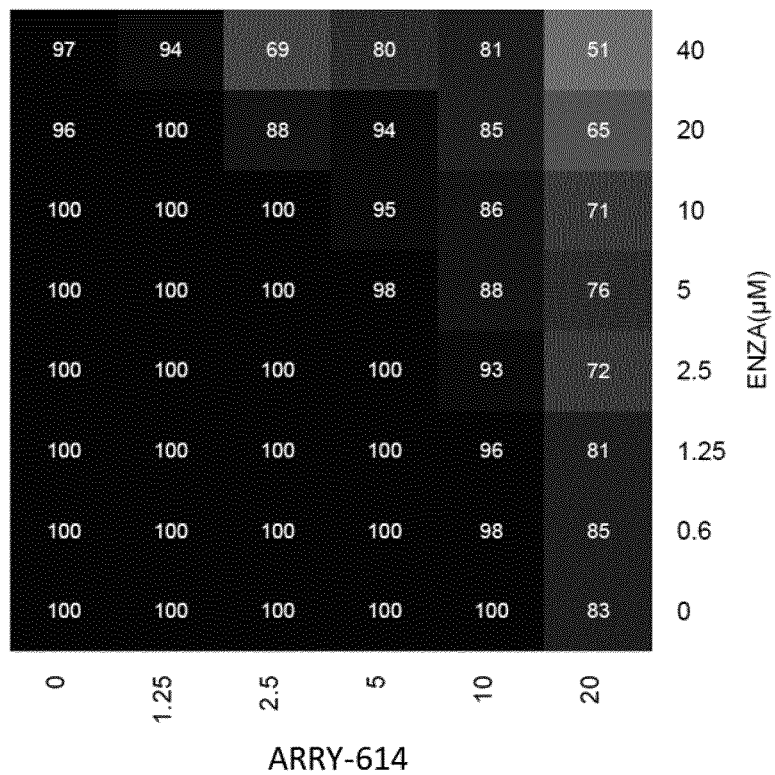
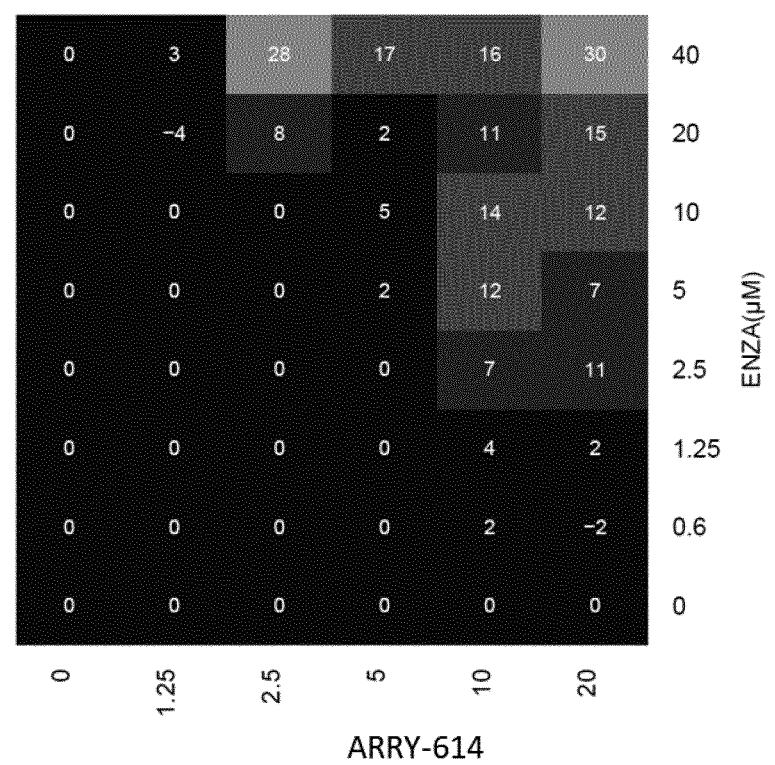
FIGURE 9D : 22Rv1 cell line

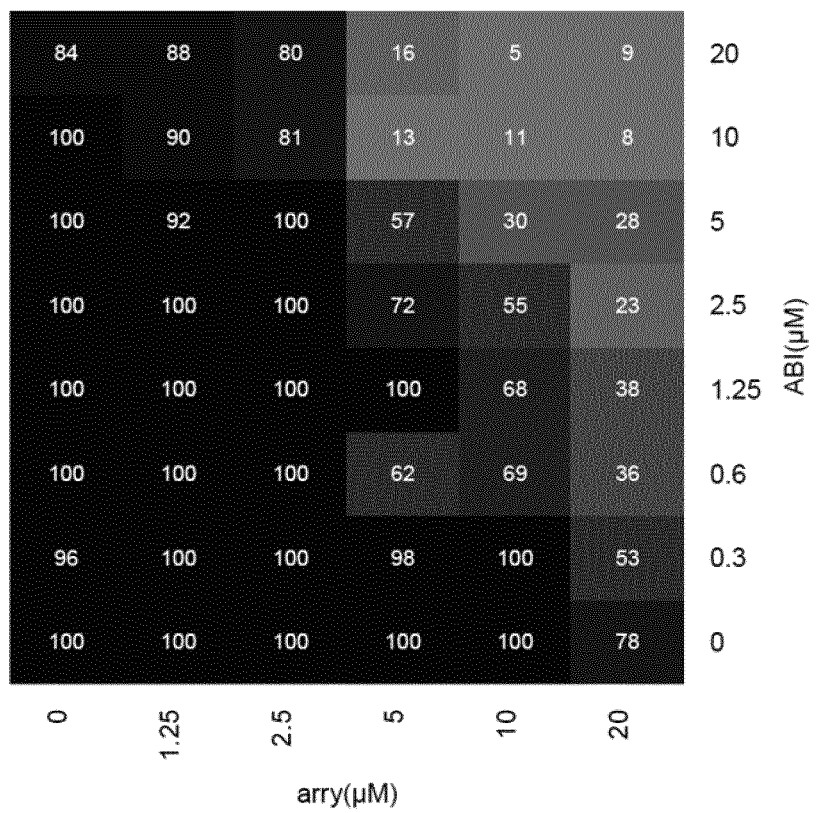
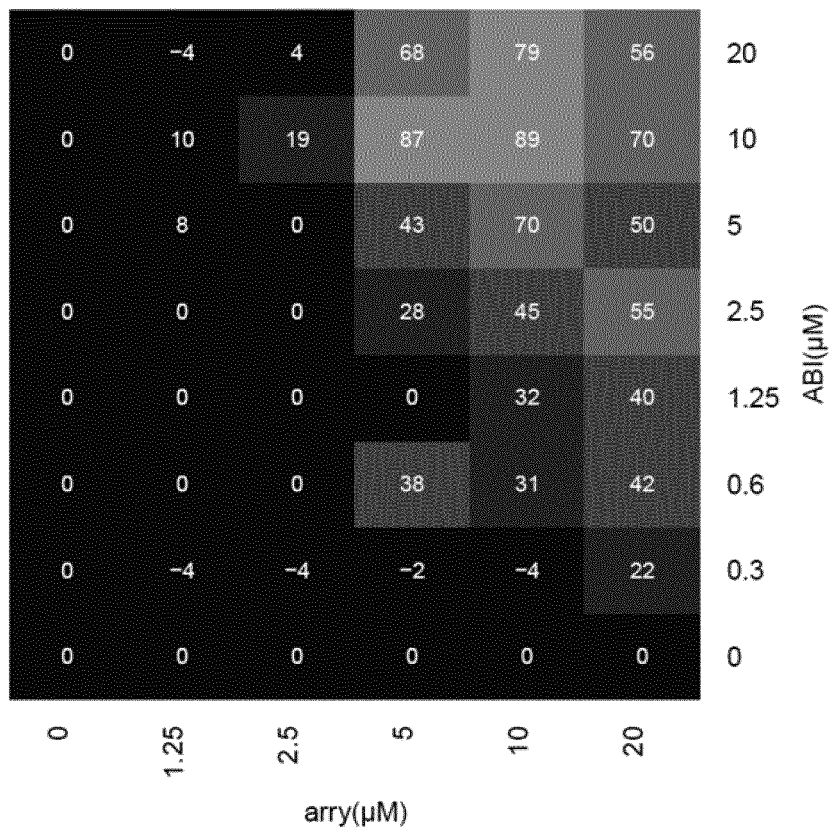
FIGURE 9E : 22Rv1 cell line

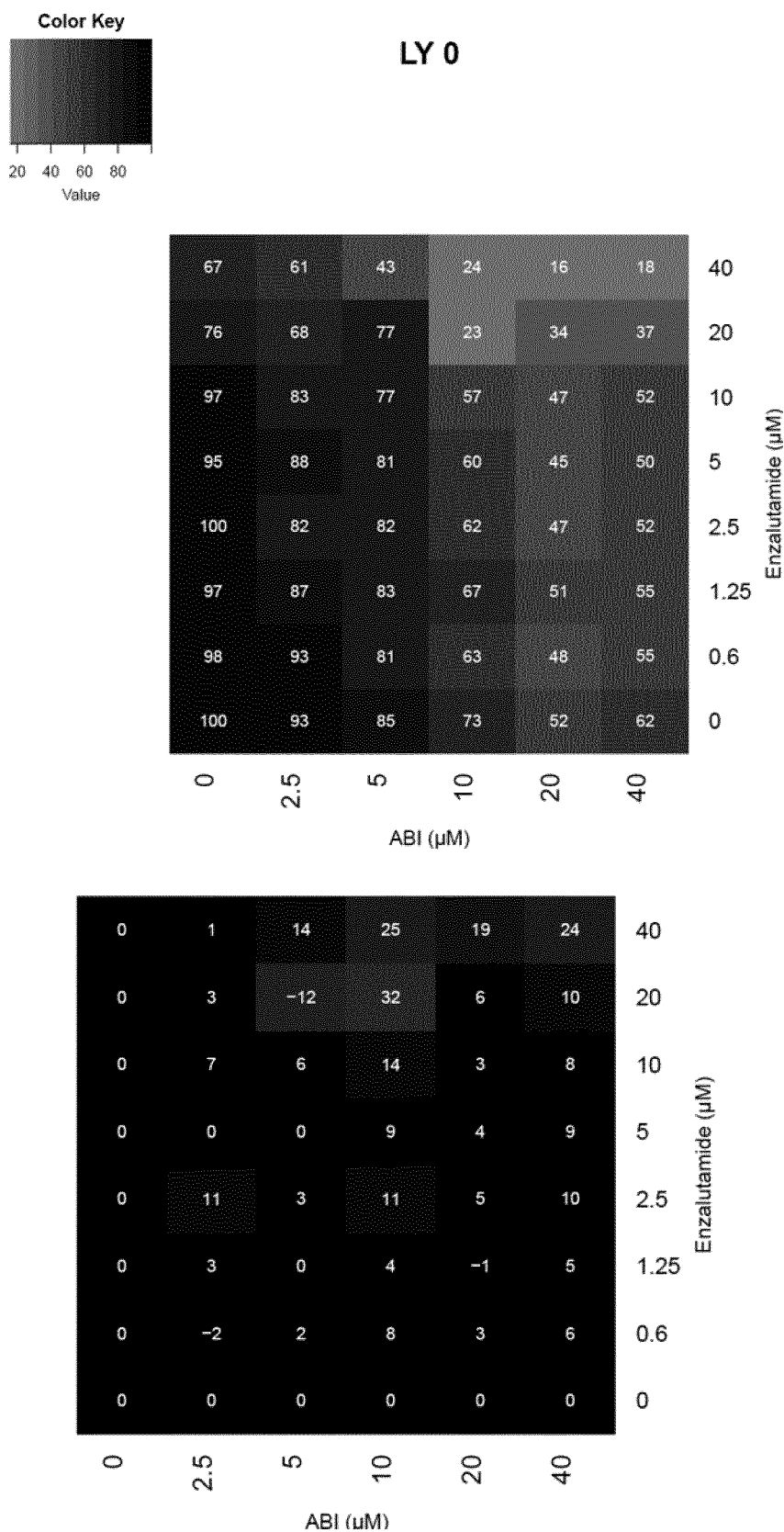
FIGURE 10A : 22Rv1 cell line

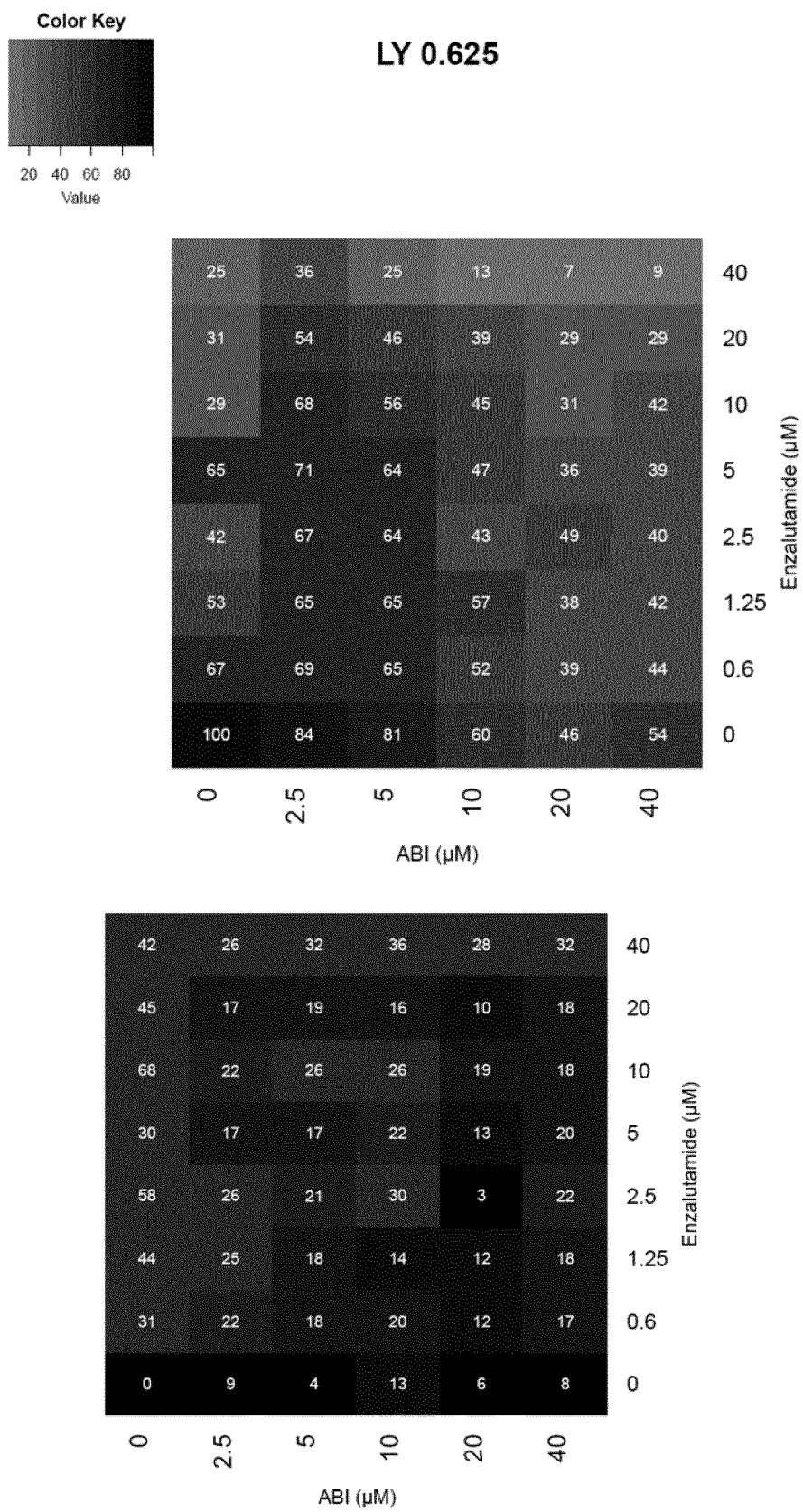
FIGURE 10B : 22Rv1 cell line

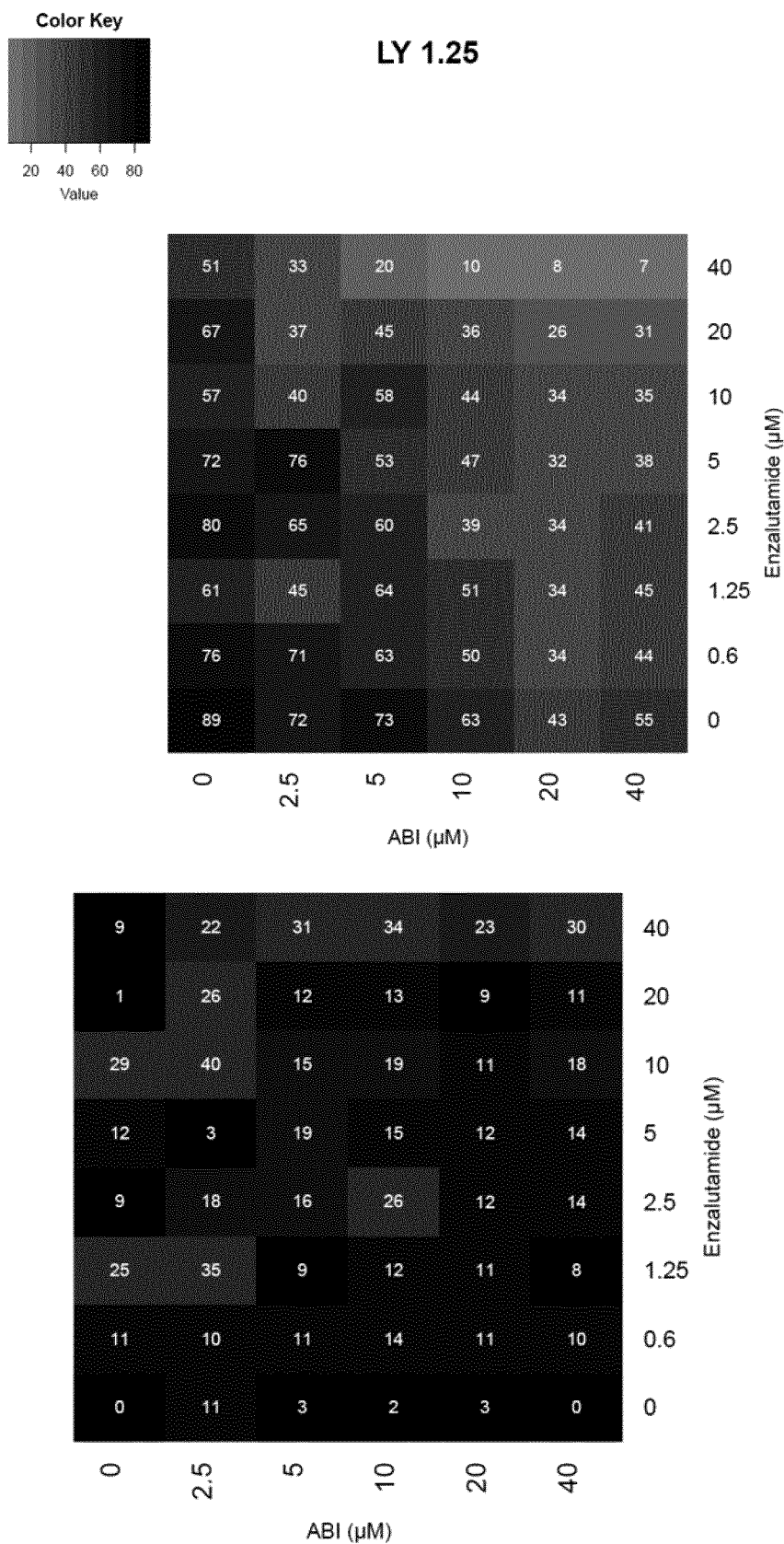
FIGURE 10C : 22Rv1 cell line

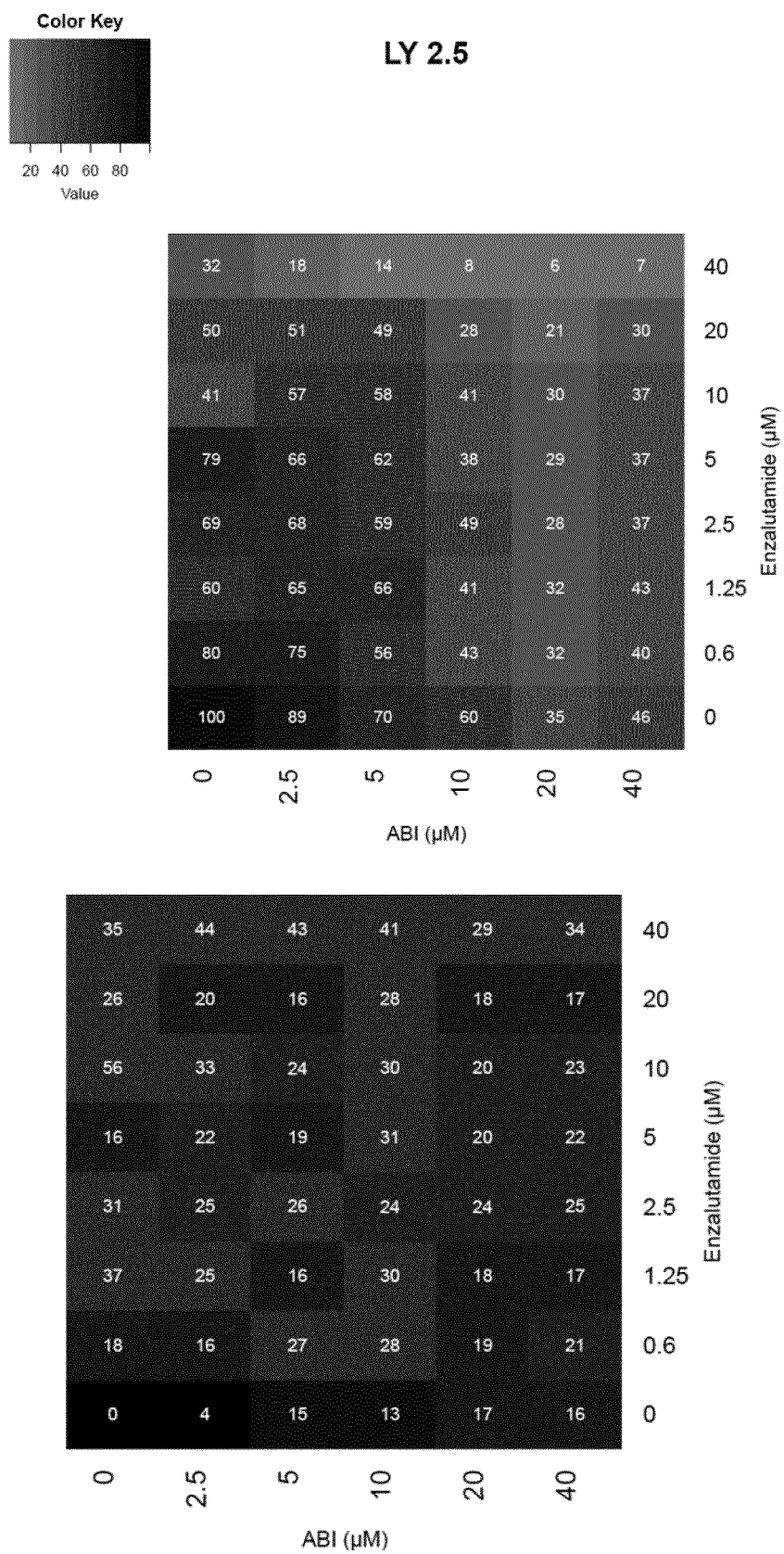
FIGURE 10D : 22Rv1 cell line

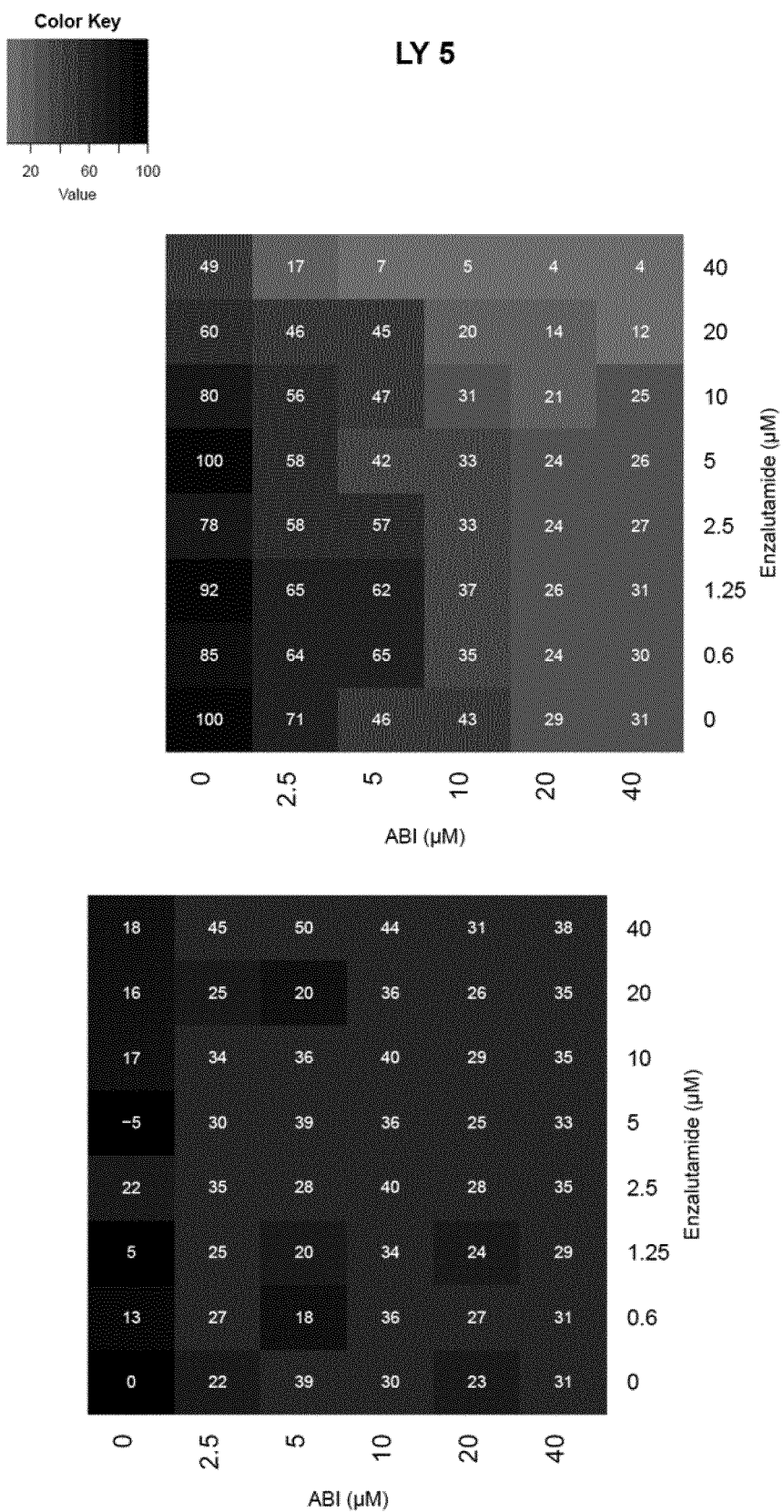
FIGURE 10E : 22Rv1 cell line

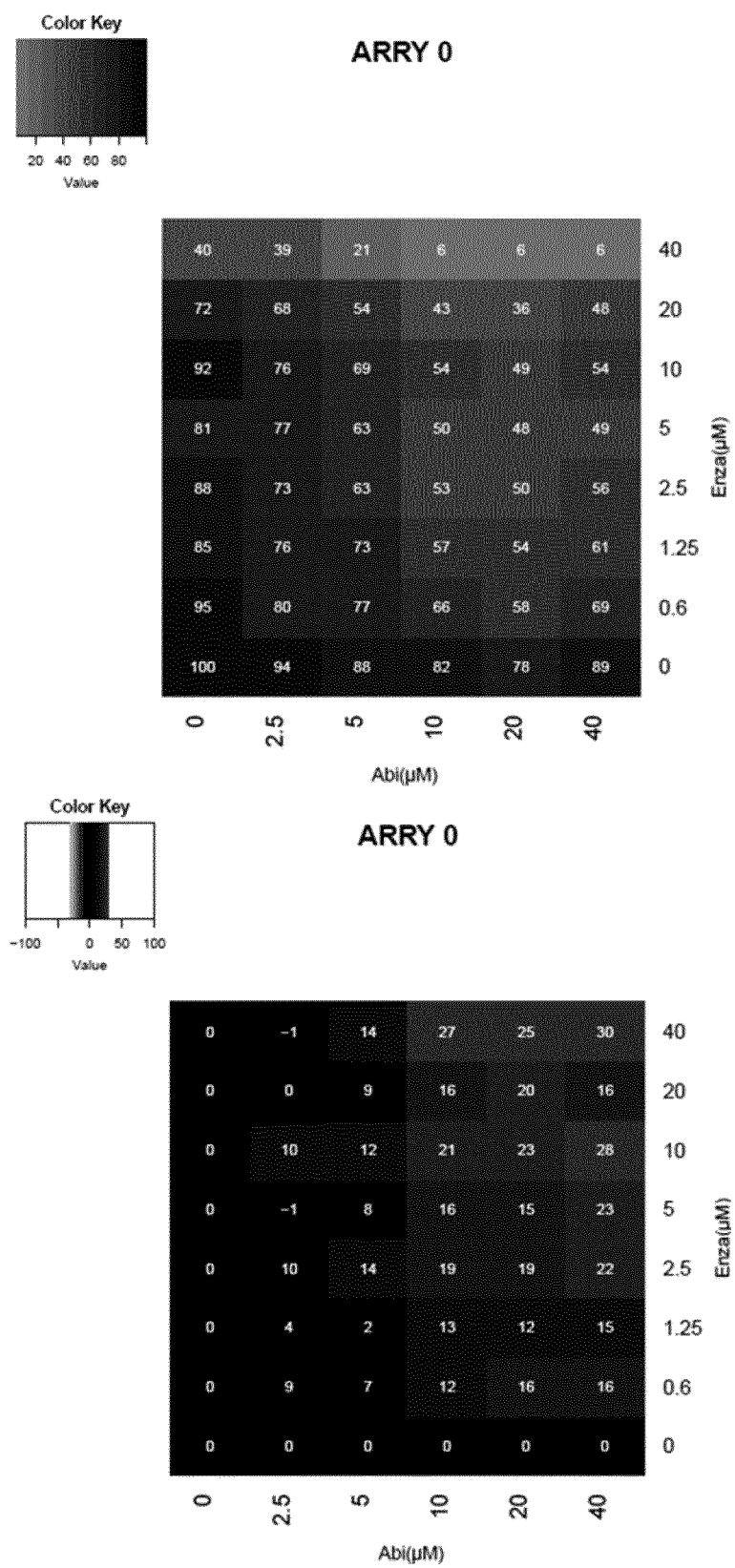
FIGURE 11A : 22Rv1 cell line

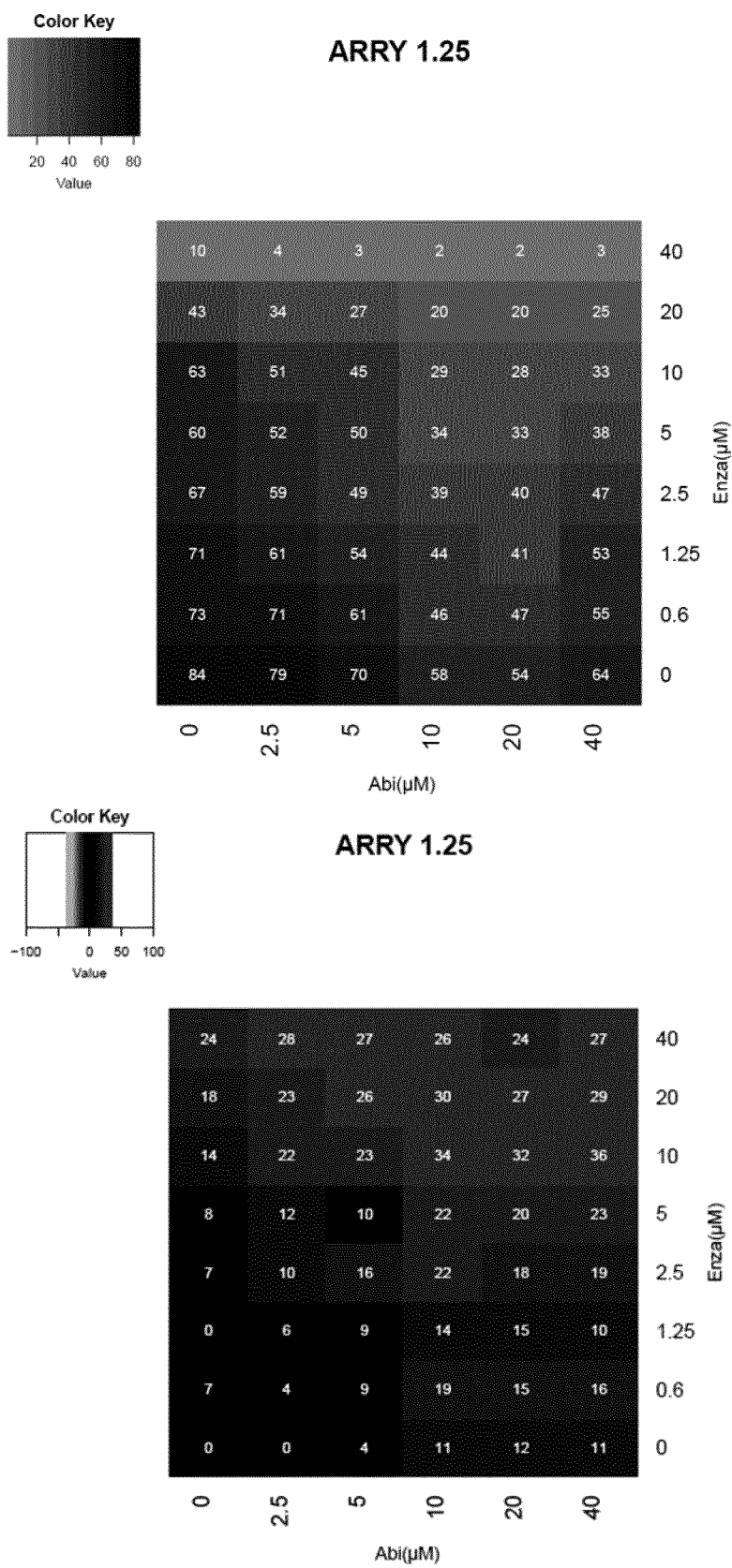
FIGURE 11B : 22Rv1 cell line

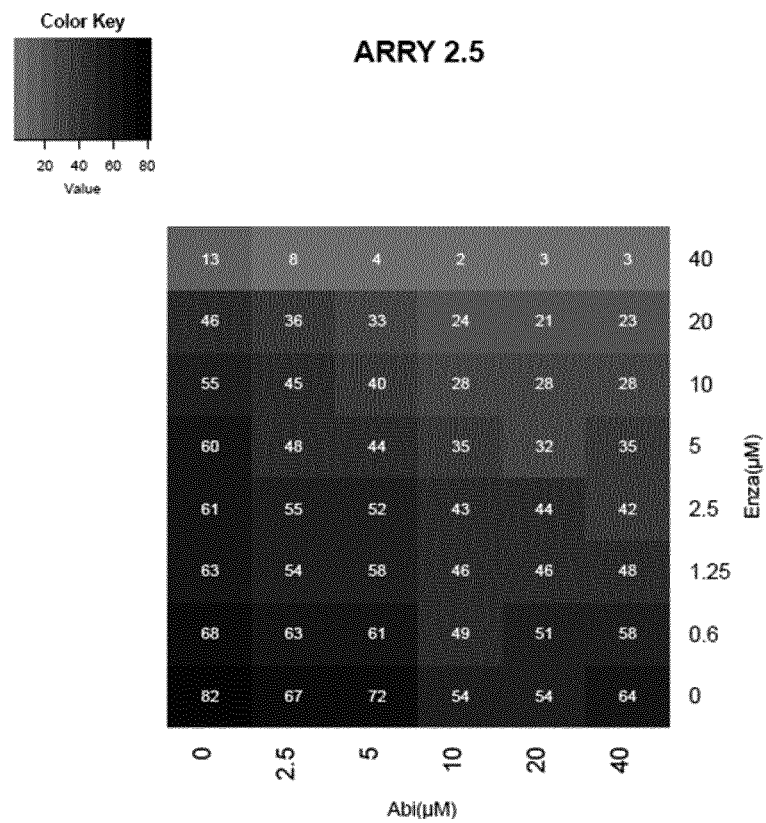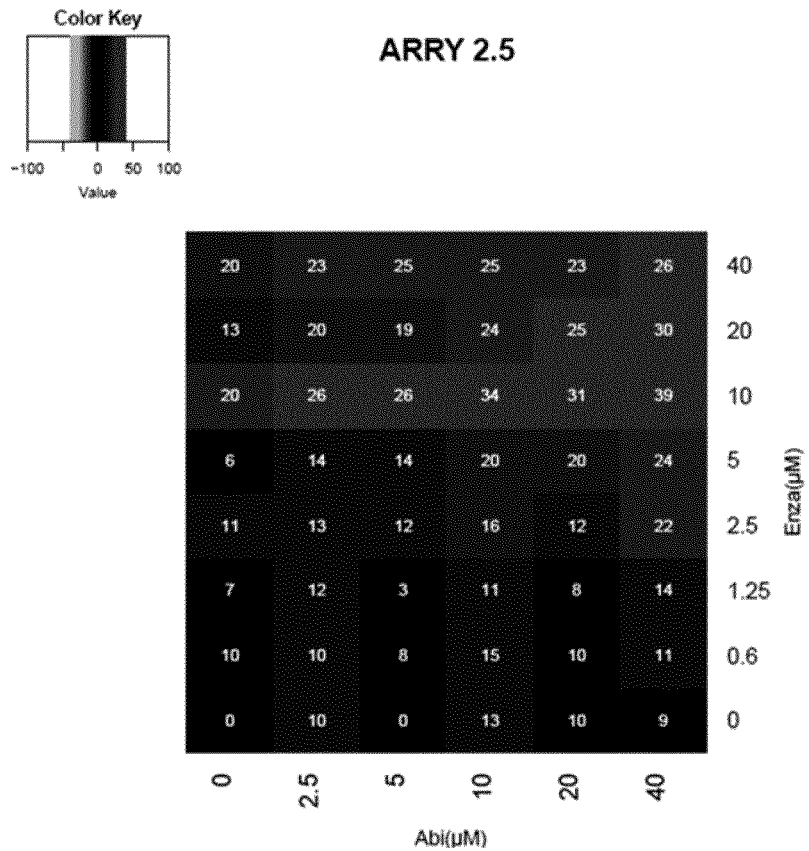
FIGURE 11C : 22Rv1 cell line

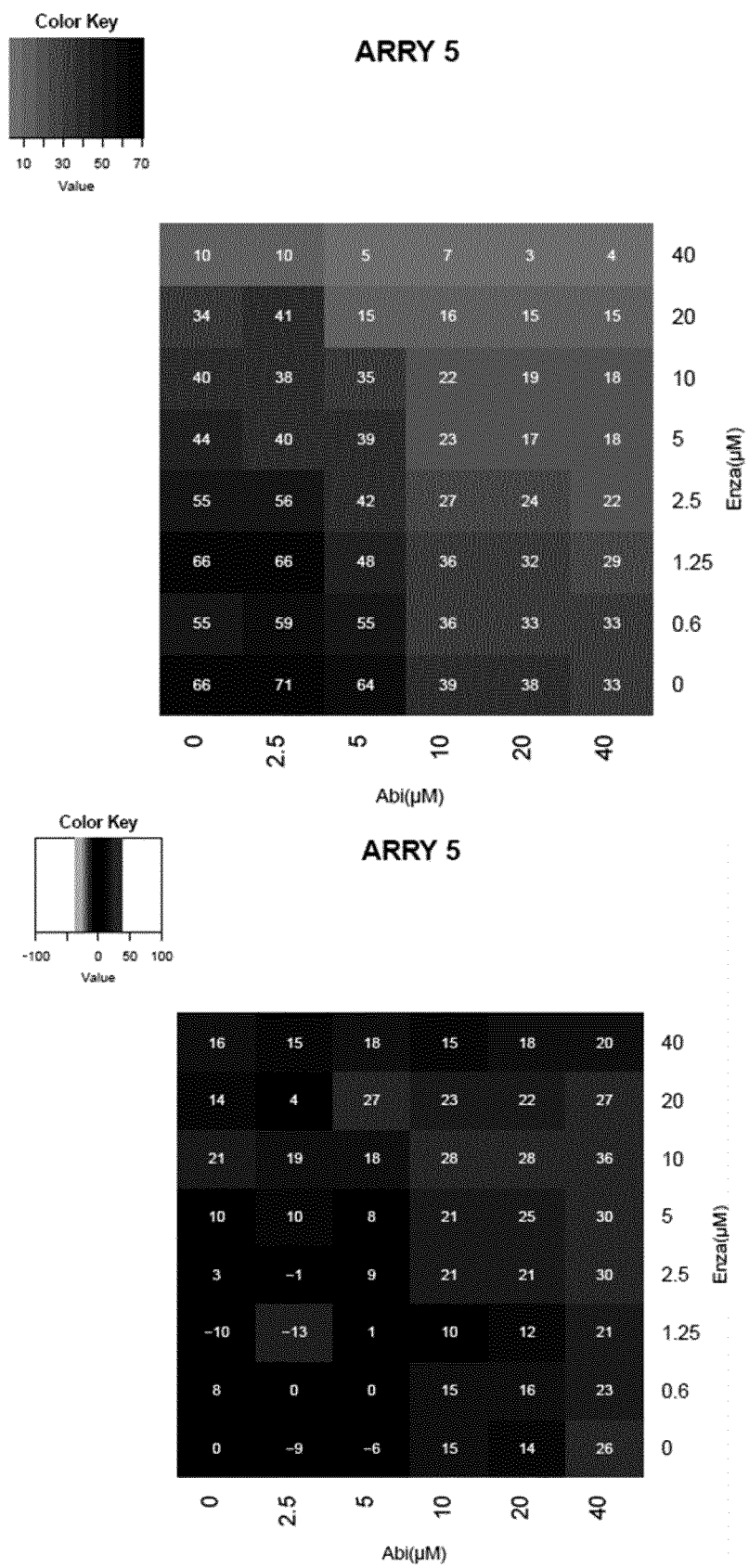
FIGURE 11D : 22Rv1 cell line

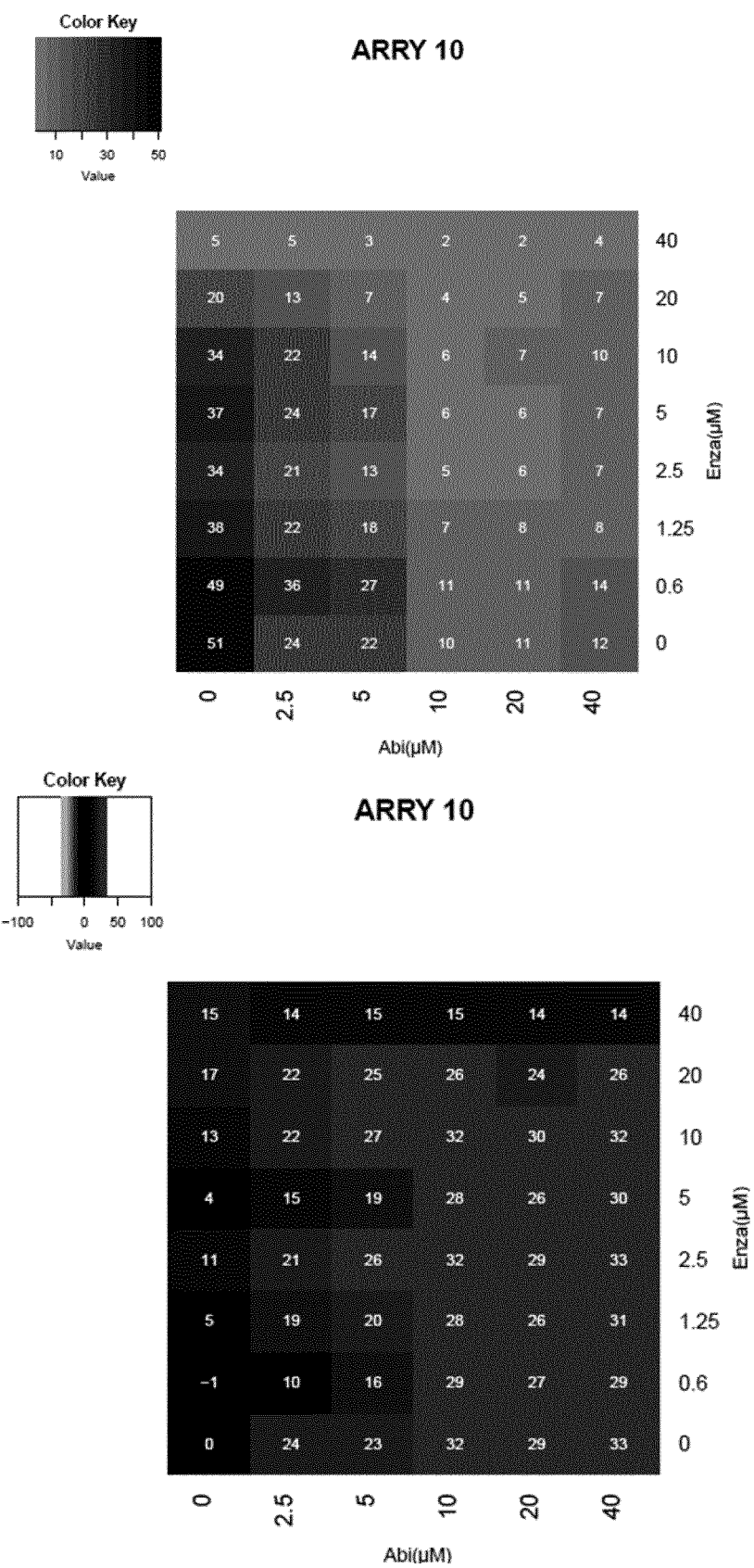
FIGURE 11E : 22Rv1 cell line

ASSOCIATION OF ACTIVES FOR TREATING PROSTATE CANCER

FIELD OF THE INVENTION

This invention relates to the treatment of prostate cancer, and more particularly castration-resistant prostate cancer. The present invention provides a combination of an inhibitor of the androgen receptor signaling pathway and of p38 inhibitor for use for treating prostate cancer in individuals wherein the prostate tumor cells express the AR-V7 variant androgen receptor protein, and for use for preventing the occurrence of resistance induced by AR-V7 for patients suffering from prostate cancer treated by an inhibitor of the androgen receptor signaling pathway. Said combination has indeed be proven to be more particularly efficient against said prostate tumor cells which are resistant to inhibitors of the androgen receptor signaling pathway and even more particularly which express the AR-V7 variant androgen receptor protein.

BACKGROUND OF THE INVENTION

Personalized medicine (i.e. targeting in a given patient specific tumor cellular pathways actually disrupted) achieves the greatest successes in few oncogene-addicted cancers but it has been by now disappointing for the large majority of cancers as results of the extremely complex interconnections between different cellular pathways and the enormous adaptive capabilities of tumor cells. Personalized treatments are in particular constantly sought for prostate cancer.

Hormonal therapy, more precisely androgen deprivation therapy (ADT) and/or Androgen-Receptor (AR) inhibition, is one of the treatment strategies offered to patients suffering from prostate cancer.

Recently, enzalutamide and abiraterone, two hormonotherapy agents targeting the AR signaling, were made available for the treatment of metastatic castration-resistant prostate cancer. Enzalutamide is a competitive androgen receptor inhibitor, while abiraterone is an androgen biosynthesis inhibitor, that inhibits 17 α-hydroxylase/C17,20-lyase. Evidence exists that enzalutamide and abiraterone improve survival in metastatic castration-resistant prostate cancer patients. However, resistance to such therapy frequently occurs after one to two years.

For example, the AR-V7 variant has been shown to mediate resistance to the treatment with enzalutamide and abiraterone in the clinical setting (Emmanuel S. Antonarakis et al "AR-V7 and resistance to enzalutamide and abiraterone in prostate cancer", N England J Med 2014 September 11; 371(11): 1028-1038). Khandrika L et al, "Hypoxia-associated p38 mitogen-activated protein kinase-mediated androgen receptor activation and increased HIF-1α levels contribute to emergence of an aggressive phenotype in prostate cancer", Oncogene 28, 1248-1260, (2009) conclude that the activation of p38 pathway is an early response to hypoxia in prostate cancer, and that inhibition of p38 MAP kinase pathway by variety of approaches abolished the hypoxia-reoxygenation induced increase of AR activity as well as the increase of survival, clonogenicity and invasiveness.

Gan et al, The Prostate 71:1158-1166, Wiley-Liss, Inc. (2011) discloses that the p38-MAPK pathway can be activated under exposure to docetaxel in prostate cancer cells, and has a critical role in the induction of resistance to the cytotoxic action of these agent, as well as in the acquisition of a more aggressive and invasive phenotype.

AN Paranjape et al, "Inhibition of FOXC2 restores epithelial phenotype and drug sensitivity in prostate cancers with stem-cell properties", Oncogene 35, 5963-5976 (2016) and patent application WO2017/117182 suggest the association of a p38 MAPK inhibitor with any anti-cancer therapy.

Document WO2017/117182 in particular mentions treatment of prostate cancer based on the rational that prostate cancer cells that are insensitive to ADT, as well as high-grade/neuroendocrine prostate tumors, are characterized by elevated FOXC2 and the absence of full-length AR expression, and that targeting FOXC2 using a well-tolerated p38-inhibitor restores epithelial attributes, full-length AR expression and ADT-sensitivity, and reduces the shedding of circulating tumor cells in vivo with significant shrinkage in the tumor mass.

Said document only refers to non-androgenic receptor expressing cancer stem cells and demonstrate the emergence in those cancer stem cells of the expression of AR after administration of a combination of enzalutamide and SB203580. However, this document is completely silent on tumor cells specifically expressing the androgen receptor AR-V7 variant.

US 2015/0209359 teaches pharmaceutical compositions including an effective amount of an antiandrogen or androgen antagonist in combination with a Plk inhibitor for reducing cancer cell proliferation or viability in a subject with cancer. However, this document does not teach a synergy between the compounds, in particular in cancer cells having developed a resistance to treatment.

None of these cited documents disclose a synergistic activity of a combination of a p38 inhibitor and an inhibitor of the androgen receptor signaling pathway, and more particularly of a p38 inhibitor and enzalutamide or abiraterone, all the more in the specific group of patients of a resistant prostate cancer associated with androgen receptor AR-V7 variant expressing cells. Expression of said AR-V7 variant may indeed be predictive for a resistance to the treatment with enzalutamide or abiraterone, for patients suffering from prostate cancer and treated with enzalutamide or abiraterone. In particular, AR-V7 variant can be present at baseline, but can also appears during enzalutamide or abiraterone therapy, in patients with a cancer resistant to castration (Antonarakis et al, "Clinical Significance of Androgen Receptor Splice Variant-7 mRNA Detection in Circulating Tumor Cells of Men With Metastatic Castration-Resistant Prostate Cancer Treated With First- and Second-Line Abiraterone and Enzalutamide", Prostate Cancer Prostatic Disease, vol 35, number 19, Jul. 1, 2017).

There is still a need for alternative or complementary anti-cancer therapies to the conventional surgical therapies and radiation therapies.

There is a continuing need for an effective therapy, and in particular personalized therapy, that delay progression or prolong life of patients suffering from prostate cancer and in particular of patients expressing resistance to hormonotherapy, in particular treated with enzalutamide or abiraterone.

Furthermore, there is a need for an effective therapy that reduces and/or postpone the occurrence of resistance by patients suffering from prostate cancer and treated by an inhibitor of the androgen receptor signaling pathway, more particularly resistance linked to a surexpression of AR-V7 variant.

In particular there remains a need for decreasing the amount of active ingredients while maintaining effective anti-prostate cancer activities thanks to synergistic combination therapies.

There also remains a need for compounds with no or limited side-effects.

SUMMARY OF THE INVENTION

The invention relates to a combination therapy for treating prostate cancer of specific groups of patients.

The invention relates more particularly to a pharmaceutical combination of an inhibitor of the androgen receptor signaling pathway and of a p38 inhibitor for use in the treatment of prostate cancer in a group of patient suffering of a prostate cancer associated with AR-V7 variant androgen receptor protein expressing cells or for preventing the occurrence of resistance in patients suffering from prostate cancer treated by an inhibitor of the androgen receptor signaling pathway.

In one embodiment, the said variant AR-V7 androgen receptor protein expressing cells are resistant to inhibitors of the androgen receptor signalling pathway.

As far as the preventive aspect is concerned, resistance to abiraterone and enzalutamide is more particularly focused on.

More generally the combination according to the present invention enables the prevention of occurrence of AR-V7 mRNA isoform of the androgen receptor of cells in patients suffering from prostate cancer as explained in more details herein after.

The invention also provides the use of a pharmaceutical combination of an inhibitor of the androgen receptor signaling pathway and of a p38 inhibitor for treating patients suffering from a prostate cancer associated with the variant AR-V7 androgenic receptor protein expressing cells.

The p38 inhibitor and the inhibitor of the androgen receptor signaling pathway may be used simultaneously, separately or may be spread out over time, and preferably simultaneously.

Accordingly, the invention relates to a pharmaceutical combination of an inhibitor of the androgen receptor signaling pathway and of a p38 inhibitor for separate administration, administration spread out over time or simultaneous administration to patients suffering from prostate cancers associated with AR-V7 variant androgen receptor protein expressing cells.

The invention further relates to a pharmaceutical composition comprising enzalutamide or abiraterone and a p38 inhibitor selected from ARRY-371797, ARRY-614 and VX-745, and at least one pharmaceutically acceptable excipient.

The invention further relates to a pharmaceutical composition comprising enzalutamide, abiraterone or apalutamide (competitive androgen receptor inhibitor, mechanism of action similar to enzalutamide) and a p38 inhibitor selected from LY2228820 and ARRY-614, and at least one pharmaceutically acceptable excipient. In other words, examples of particular combinations more particularly suitable in the framework of the present application are enzalutamide and LY2228820, enzalutamide and ARRY-614, abiraterone and LY2228820, abiraterone and ARRY-614, apalutamide and LY2228820 and apalutamide and ARRY-614.

In another embodiment, the invention relates to a pharmaceutical combination of a p38 inhibitor, in particular ARRY-371797, ARRY-614 or VX-745, and enzalutamide or abiraterone, for separate administration, administration spread out over time or simultaneous administration to patients suffering from prostate cancers wherein prostate tumour cells express the AR-V7 variant androgen receptor protein.

In a particular embodiment, the invention relates to a pharmaceutical combination of a p38 inhibitor, in particular LY2228820 or ARRY-614, and respectively enzalutamide, abiraterone or apalutamide for separate administration, administration spread out over time or simultaneous administration to patients suffering from prostate cancers wherein prostate tumour cells express the AR-V7 variant androgen receptor protein.

The pharmaceutical combination comprises an effective amount of p38 inhibitor and an effective amount of an inhibitor of the androgen receptor signaling pathway.

The invention further relates to the use of a p38 inhibitor for restoring the sensitivity to androgen-deprivation therapy (ADT) in patients suffering from prostate cancers having acquired a resistance to ADT following a treatment with an inhibitor of the androgen receptor signaling pathway and wherein the prostate tumour cells express the AR-V7 variant androgen receptor protein, wherein said inhibitor of the androgen receptor signaling pathway may more particularly be chosen among enzalutamide, abiraterone and apalutamide and wherein said p38 inhibitor may more particularly be chosen among LY2228820 and ARRY-614.

The invention further describes a method for determining whether an individual affected with prostate cancer is eligible to a prostate cancer treatment with a pharmaceutical combination as defined in any one of the preceding claims, wherein said method comprises the step of determining whether a tumor tissue sample previously obtained from the said individual expresses the AR-V7 variant androgen receptor protein.

In the framework of the present invention, the following definitions may be given:
  effective amount: amount of a pharmaceutical compound which produces an effect on the tumour treated;
  the separate administration, simultaneous administration or administration spread out over time of a medicinal combination means that the elementary constituents of the combination, can be administered at the same time, each in one go at distinct moments, or repeatedly, or else at different moments, in particular during cycles. The elementary constituents can, in order to do this, be formulated as mixtures, only if they are administered simultaneously, or else formulated separately for the other administration schemes;
  As used herein, the term "pharmaceutically acceptable" refers to those compounds, materials, excipients, compositions or dosage forms which are, within the scope of sound medical judgment, suitable for contact with the tissues of human beings and animals without excessive toxicity, irritation, allergic response or other problem complications commensurate with a reasonable benefit/risk ratio.

In the framework of the present invention a "p38 MAPK inhibitor" is equivalent to a "p38 inhibitor".

For the sake of simplicity, abiraterone, enzalutamide and apalutamide will be collectively hereinafter referred to as "inhibitor of the androgen receptor signaling pathway".

In the framework of the present invention a "double combination" means a pharmaceutical composition or kit comprising an inhibitor of androgen receptor signaling pathway, in particular selected from apalutamide, enzalutamide and abiraterone and a p38 inhibitor, and in particular LY2228820 or ARRY-614 and a "triple combination" means a pharmaceutical composition or kit comprising two inhibitors of androgen receptor signaling pathway selected from apalutamide, enzalutamide and abiraterone and a p38 inhibitor, and in particular LY2228820 or ARRY-614.

According to another one of its aspects, the present invention relates to a pharmaceutical composition comprising at least two inhibitors of the androgen receptor signaling pathway and at least one p38 inhibitor, wherein said inhibitor of the androgen receptor signaling pathway may more particularly be chosen among enzalutamide, abiraterone and apalutamide and wherein said p38 inhibitor may more particularly be chosen among LY2228820 and ARRY-614.

According to another one of its aspects, the present invention relates to a pharmaceutical composition comprising at least two inhibitors of the androgen receptor signaling pathway and at least one p38 inhibitor for use in the treatment of prostate cancer in individuals wherein the prostate tumor cells express the AR-V7 variant androgen receptor protein or for preventing the occurrence of resistance in patients suffering from prostate cancer treated by an inhibitor of the androgen receptor signaling pathway, wherein said inhibitor of the androgen receptor signaling pathway may more particularly be chosen among enzalutamide, abiraterone and apalutamide and wherein said p38 inhibitor may more particularly be chosen among LY2228820 and ARRY-614.

BRIEF DESCRIPTION OF THE FIGURES

FIG. 4: In vitro double combination study and synergism 2D-analysis for the combination of enzalutamide and the p38 inhibitor SB202190. Experimental survival data (A) and synergism (B) matrices for different prostate cancer cell lines LNCaP and 22Rv1 (4A and 4B) incubated with the combination at the indicated concentrations. In the experimental data matrices, values indicate the percentage of surviving cells. In the synergism matrices, the "shades of grey scale" is used to indicate antagonist or additive combinations (black) and synergistic combinations (gray, with lighter gray corresponding to more intense synergism) (Example 2).

FIG. 8: In vitro double combination study and synergism 2D-analysis for the combination of enzalutamide and the p38 inhibitor LY2228820 (FIG. 8A) or ARRY-614 (FIG. 8B). Experimental survival data and synergism matrices for 22Rv1 cells incubated with the combination at the indicated concentrations. In the experimental data matrices, values indicate the percentage of surviving cells. In the synergism matrices, the shades of grey scale is used to indicate antagonist or additive combinations (black) and synergistic combinations (gray, with lighter gray corresponding to more intense synergism) (Example 5).

FIG. 9: In vitro double combination study and synergism 3D-analysis for the combination of enzalutamide and the p38 inhibitor LY2228820 (FIG. 9A), abiraterone and LY2228820 (FIG. 9B), apalutamide and LY2228820 (FIG. 9C), enzalutamide and the p38 inhibitor ARRY-614 (FIG. 9D) and abiraterone and ARRY-614 (FIG. 9E). Experimental survival data and synergism matrices for 22Rv1 cells incubated with the combination at the indicated concentrations. In the experimental data matrices, values indicate the percentage of surviving cells. In the synergism matrices, the shades of grey scale is used to indicate antagonist or additive combinations (black) and synergistic combinations (gray, with lighter gray corresponding to more intense synergism) (Example 6).

FIG. 10: In vitro triple combination study and 3D-synergism analysis on 22Rv1 cells for the combination of enzalutamide and abiraterone in the absence of p38 inhibitor LY2228820 (FIG. 10A), in the presence of 0.625 µM of LY2228820 (FIG. 10B), in the presence of 1.25 µM of LY2228820 (FIG. 10C), the presence of 2.5 µM of LY2228820 (FIG. 10D) and in the presence of 5.0 µM of LY2228820 (FIG. 10E). Experimental survival data and synergism matrices for 22Rv1 cells incubated with the combination at the indicated concentrations. In the experimental data matrices, values indicate the percentage of surviving cells. In the synergism matrices, the shades of grey scale is used to indicate antagonist or additive combinations (black) and synergistic combinations (gray, with lighter gray corresponding to more intense synergism) (Example 7).

FIG. 11: In vitro triple combination study and 3D-synergism analysis on 22Rv1 cells for the combination of enzalutamide and abiraterone in the absence of p38 inhibitor ARRY-614 (FIG. 11A), in the presence of 1.25 µM of ARRY-614 (FIG. 11B), the presence of 2.5 µM of ARRY-614 (FIG. 11C), in the presence of 5.0 µM of ARRY-614 (FIG. 11D), and in the presence of 10.0 µM of ARRY-614 (FIG. 11E). Experimental survival data and synergism matrices for 22Rv1 cells incubated with the combination at the indicated concentrations. In the experimental data matrices, values indicate the percentage of surviving cells. In the synergism matrices, the shades of grey scale is used to indicate antagonist or additive combinations (black) and synergistic combinations (gray, with lighter gray corresponding to more intense synergism) (Example 7).

DETAILED DESCRIPTION OF THE INVENTION

Figure 1:
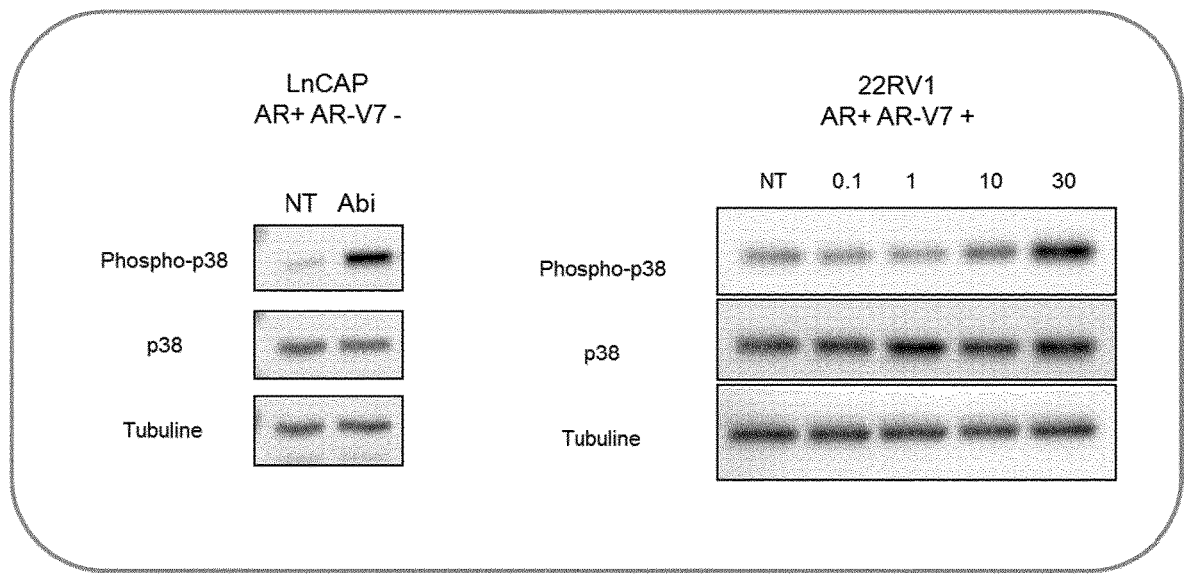
FIG. 1: Abiraterone induces p38 activation. Prostate cancer cells LNCaP (Androgen Receptor expressing cells) were treated with abiraterone (30 µM). Prostate cancer cells 22Rv1 (Androgen Receptor and AR-V7 expressing cells) were treated with 0.1, 1.0, 10.0 and 30.0 µM abiraterone during 24 hours. Protein were extracted and subjected to western blot analysis using anti-phospho-p38, anti-p38 and anti-tubulin antibodies. (Example 1)

As explained in Antonarakis et al, "Clinical Significance of Androgen Receptor Splice Variant-7 mRNA Detection in Circulating Tumor Cells of Men With Metastatic Castration-Resistant Prostate Cancer Treated With First- and Second-Line Abiraterone and Enzalutamide", Prostate Cancer Prostatic disease, vol 35, number 19, Jul. 1, 2017, AR-V7 is an abnormally spliced mRNA isoform of the androgen receptor, producing a protein product lacking the C-terminal ligand-binding domain but retaining the transcriptionally active N-terminal domain. Despite its inability to bind ligand (eg, dihydrotestosterone), AR-V7 remains constitutively active in a ligand independent manner and is capable of driving metastatic castration-resistant prostate cancer (CRPC) growth.

Said article has confirmed at a larger scale that patients for which detection of androgen receptor splice variant AR-V7 in circulating tumor cells (CTCs) have inferior clinical outcomes compared to patients for which no detection of androgen receptor splice variant AR-V7 in circulating tumor cells (CTCs) have occurred.

The present invention is based on the inventor's experiments showing that the association of a p38 inhibitor and at least an inhibitor of the androgen receptor signaling pathway acts synergistically in reducing proliferation of prostate cancer cell, as thereafter illustrated in the examples.

As it is shown in the examples herein, the inventors have found that a pharmaceutical combination of at least an inhibitor of the androgen receptor signaling pathway and of a p38 inhibitor causes a synergistic activity in Androgen Receptor positive cell lines such as LNCaP and 22Rv1.

As it will be apparent from the examples herein after, the inventors have also proven that p38 inhibitors, and in particular SB202190, surprisingly inhibit the expression of the AR-V7 variant when they are combined with abiraterone or enzalutamide (example 4).

They have further shown that a combination of abiraterone or enzalutamide with the p38 inhibitor SB202190 is highly efficient in vivo, in a preclinical xenograft model (example 3).

Results are also provided demonstrating by microscope observation that the in vitro administration of a combination of an inhibitor of the androgen receptor signaling pathway and a p38 inhibitor reduced the expression of the AR-V7 variant in Androgen Receptor expressing cells and AR-V7 (Example 8).

The inventors have furthermore proven that the presence of a p38 inhibitor prevents the expression of AR-V7 when LNCaP cells are chronically treated with an androgen receptor signaling pathway whereas they have stated the appearance of AR-V7 and the occurrence of resistance when treated with an androgen receptor signaling pathway alone (Example 9).

With respect to the teaching of document WO2017/117182, it is worth to underline that it relies on the sensitization of stem cells via the appearance of AR while the present invention relates to the sensitization of mature tumor cells via the decrease in the expression of AR-V7, the expression of AR remaining unchanged, as it will be more apparent in the examples.

A pharmaceutical combination conform to the present invention allows to restore the sensitivity to ADT, and in particular on Androgen Receptor expressing cells and AR-V7 cell lines, as shown in FIGS. 3, 4, 5, 6, 7, 8, 9, 10, 11 and 12.

Inhibitor of the Androgen Receptor Signaling Pathway

Inhibitors of the androgen receptor signaling pathway are also called "hormonotherapy agents targeting the Androgenic Receptor" or "androgen biosynthesis inhibitors" or "androgen deprivation compounds".

Examples of inhibitors of the androgen receptor signaling pathway for use in the present invention include but are not limited to enzalutamide, apalutamide, bicalutamide, nilutamide, flutamide, abiraterone, ketokonazole, darolutamide, orteronel, and more particularly enzalutamide and abiraterone. According to a particularly preferred embodiment, inhibitors of the androgen receptor signaling pathway according to the invention are chosen from enzalutamide, abiraterone and apalutamide.

Enzalutamide is an inhibitor of the androgen receptor signaling pathway that blocks several steps in the androgen receptor signaling pathway.

Figure 2:
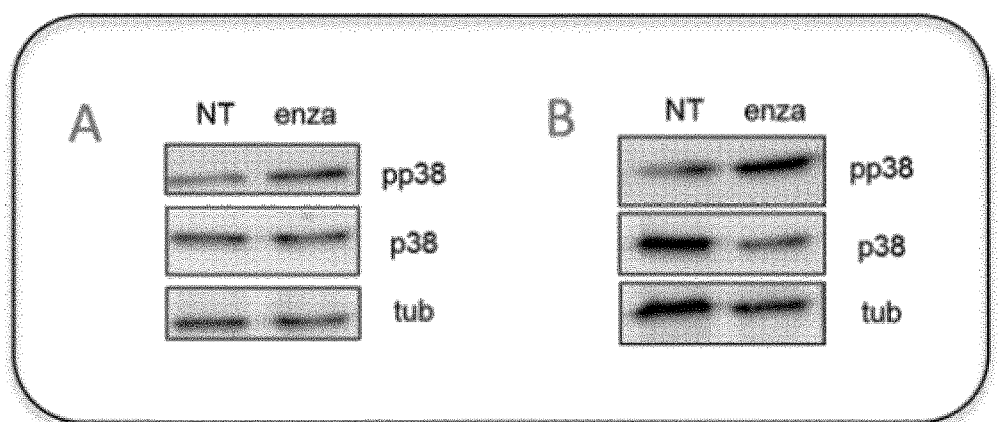
FIG. 2: Enzalutamide induces p38 activation. A: LNCaP human prostate cells (Androgen Receptor expressing cells) were treated by enzalutamide (35.0 µM) during 24 h00. Phosphorylation p38 was assessed. Tubuline and non-phosphorylated proteins were stained as a loading control. B: same experiment with the Androgen Receptor and AR-V7 expressing 22Rv1 human prostate cancer cells (Example 1).

As shown in the examples (see example 1 and FIG. 2) the inventors have proven that abiraterone activates the MAPK p38 in prostate cancer cells.

Abiraterone, in particular under the form of abiraterone acetate, has already been positively tested in metastatic prostate cancer.

Abiraterone is a first-in class inhibitor of cytochrome P-450c17, a critical enzyme in extragonadal and testicular androgen synthesis. Abiraterone is a potent inhibitor of CYP17A1, one of the rate-limiting enzymes in the biosynthesis of testosterone from cholesterol in adrenal cortex and in prostate cancer cells.

As shown in the examples (see example 1 and FIG. 1) the inventors have proven that abiraterone activates the MAPK p38 in prostate cancer cells.

Apalutamide is another inhibitor of the androgen receptor signaling pathway known in the art.

P38 inhibitor

Examples of p38 inhibitors for use in the present invention include but are not limited to LY2228820, LY3007113, SCIO-469, ARRY-371797, ARRY-614, PH-797804, RO4402257 (pamapimod), SB681323, VX-745, BMS-582949, GS856553, GW856553 (losmapimod) and VX-702, more particularly ARRY-371797, ARRY-614 and VX-745. According to a particularly preferred embodiment, p38 inhibitors used according to the invention are chosen from LY2228820 and ARRY-614.

SB202190 and SB203580 are also p38 inhibitors which are not clinically used but commonly used for experimental data, as in the present examples herein after.

Androgen Receptor Protein Expressing Cells

Examples of androgen receptor protein expressing cell lines in the prostate cancer include but are not limited to LNCaP, 22Rv1, MDA PCa 2b, VCaP, LNCaP95 and in particular to LNCaP (Androgen Receptor expressing cells, AR-V7−) and 22Rv1 (Androgen Receptor expressing cells, AR-V7+) as used in the following examples.

Method for Determining Whether an Individual is Eligible to Prostate Cancer Treatment Implementing the Pharmaceutical Combination According to the Present Invention Any method known to the man skilled in the art may be used.

Such a method may typically comprise the step of testing the prostate cancer cells of a patient, and namely from the circulating tumor cells (CTCs) or from blood RNA of said patient, for determining whether the prostate cancer cell lines express the AR-V7 androgenic receptor variant.

As detailed in Emmanuel S. Antonarakis et al "AR-V7 and resistance to enzalutamide and abiraterone in prostate cancer", N England J Med 2014 Sep. 11; 371(11): 1028-1038, a quantitative reverse-transcriptase-polymerase-chain-reaction assay may be used to evaluate AR-V7 in circulating tumor cells from the considered patients.

Detection of androgen receptor variant AR-V7 may be performed according to techniques as mentioned in Antonarakis et al, "Clinical Significance of Androgen Receptor Splice Variant-7 mRNA Detection in Circulating Tumor Cells of Men With Metastatic Castration-Resistant Prostate Cancer Treated With First- and Second-Line Abiraterone and Enzalutamide", Prostate Cancer Prostatic disease, vol 35, number 19, Jul. 1, 2017.

In particular, the detection may be performed from the circulating tumor cells (CTCs) or from blood RNA of the patients.

Capture of CTCs can be performed using the EpCAM-based ProstateCancerSelect kit, and mRNA expression analyses can be performed using the Prostate-CancerDetect kit with multiplexed reverse-transcription polymerase chain reaction primers to establish the presence or absence of CTCs. Custom primers can be designed to detect full-length androgen receptor (AR-FL) mRNA and AR-V7 mRNA, as described previously. The relative abundance of AR-V7 can be determined by calculating the ratio of AR-V7 transcript to AR-FL transcript.

In other embodiments, measurement of the expression of the androgen receptor variant AR-V7 may be performed by methods of detection of the AR-V7 protein, as it is shown in the examples herein.

In some embodiments, a sample of prostate cancer cells that has been collected from a prostate cancer patient is incubated with a detectable anti-AR-V7 antibody, so as to provide an assay sample, and the said assay sample is then subjected to detection of AR-V7 positive cells, preferably by a well-known FACS method of cell sorting. The presence of AR-V7 protein in the said assay sample is indicative that the said prostate cancer patient is responsive to a therapeutic treatment with a combination of an inhibitor of the androgen receptor signaling pathway and of a p38 inhibitor. Detection of the AR-V7 protein expression in a sample of prostate cancer cells previously collected from a prostate patient may be performed by methods, such as described by Scher et al. (2016, JAMA Oncol., Vol. 2 (n° 11): 1441-1449).

In some other embodiments, the detection of the expression of the androgen receptor variant AR-V7 protein, a sample of prostate cancer cells that has been collected from a prostate cancer patient may be subjected to a protein extraction method before performing detection of the AR-V7 variant protein by a method of Western blot, using an anti-AR-V7 antibody, as it is shown in the examples. The presence of AR-V7 protein in the said protein extract is indicative that the said prostate cancer patient is responsive to a therapeutic treatment with a combination of an inhibitor of the androgen receptor signaling pathway and of a p38 inhibitor.

It may be used the monoclonal anti-AR-V7 antibody commercialized by Abcam under the reference number [EPR15656] ab198394.

It may also be used the polyclonal anti-ARV-7 antibody commercialized by Cell Signalling Technology Inc. under the reference number #68492.

Combination and Administration Scheme

Prostate cancer is classically treated in a first stage by androgen-deprivation therapy (ADT). Castration-resistant prostate cancer is defined by disease progression despite androgen-deprivation therapy (ADT). Said disease evolution is characterized by a continuous rise in serum levels of prostate-specific antigen (PSA), progression of pre-existing disease, or appearance of new metastases.

Novel Hormonal Therapies (NHT) are then commonly considered for treating patients suffering from said castration-resistant prostate cancer, in particular with abiraterone or enzulatamide. According to the present application, the term "Castration-resistant prostate cancer" can be encountered under other terms "Advanced PCA", "hormone-resistant PCA (HRPC)", "androgen-insensitive PCA", and most recently, the terms "castration-resistant" or "castration-recurrent", which are here considered as equivalent.

As regards the combination according to the present invention, it may in particular be used for treating patients suffering from said Castration-resistant prostate cancer.

Alternatively, it may be used in a preventive way, so that the patient does not develop resistance to inhibitor of the androgen receptor signaling pathway. Therefore, said combination may also be used prior to a treatment with an inhibitor of the androgen receptor signaling pathway, and even during the first stage by androgen-deprivation therapy (ADT).

As shown in the examples, the efficacy of various double and triple combinations has been proven on various cell lines expressing or not AR-V7, including on a preventive mode, i.e. the p38 inhibitor allowing the restoration of the sensitivity of cancer cells to androgen deprivation therapy after occurrence of a resistance (example 9).

According to a particular embodiment, the invention relates to a double combination for use in the treatment of prostate cancer for preventing the occurrence of resistance in patients suffering from prostate cancer treated by an inhibitor of the androgen receptor signaling pathway.

According to a further particular embodiment, the invention relates to a triple combination for use in the treatment of prostate cancer in individuals wherein the prostate tumor cells express the AR-V7 variant androgen receptor protein.

According to a preferred embodiment, when the inhibitor of the androgen receptor signaling pathway is enzalutamide, the p38 inhibitor may be chosen from LY2228820 and ARRY-614.

According to another preferred embodiment, when the inhibitor of the androgen receptor signaling pathway is abiraterone, the p38 inhibitor may be chosen from LY2228820 and ARRY-614.

According to another preferred embodiment, when the inhibitor of the androgen receptor signaling pathway is apalutamide, the p38 inhibitor may be chosen from LY2228820 and ARRY-614.

According to preferred embodiment, a pharmaceutical composition or a kit according to the invention comprises apalutamide and enzalutamide as inhibitors of the androgen receptor signaling pathway, and LY2228820 as the p38 inhibitor.

According to preferred embodiment, a pharmaceutical composition or a kit according to the invention comprises apalutamide and enzalutamide as inhibitors of the androgen receptor signaling pathway, and ARRY-614 as the p38 inhibitor.

According to preferred embodiment, a pharmaceutical composition or a kit according to the invention comprises apalutamide and abiraterone as inhibitors of the androgen receptor signaling pathway, and LY2228820 as the p38 inhibitor.

According to preferred embodiment, a pharmaceutical composition or a kit according to the invention comprises apalutamide and abiraterone as inhibitors of the androgen receptor signaling pathway, and ARRY-614 as the p38 inhibitor.

According to preferred embodiment, a pharmaceutical composition or a kit according to the invention comprises enzalutamide and abiraterone as inhibitors of the androgen receptor signaling pathway, and LY2228820 as the p38 inhibitor.

According to preferred embodiment, a pharmaceutical composition or a kit according to the invention comprises enzalutamide and abiraterone as inhibitors of the androgen receptor signaling pathway, and ARRY-614 as the p38 inhibitor.

In a most preferred embodiment, a pharmaceutical combination or kit according to the invention comprises:
  enzalutamide as the inhibitor of the androgen receptor pathway and LY2228820 as the p38 inhibitor,
  apalutamide as the inhibitor of the androgen receptor pathway and LY2228820 as the p38 inhibitor,
  abiraterone as the inhibitor of the androgen receptor pathway and LY2228820 as the p38 inhibitor,
  enzalutamide as the inhibitor of the androgen receptor pathway and ARRY-614 as the p38 inhibitor,
  abiraterone as the inhibitor of the androgen receptor pathway and ARRY-614 as the p38 inhibitor, or
  apalutamide as the inhibitor of the androgen receptor pathway and ARRY-614 as the p38 inhibitor.

In another most preferred embodiment, a pharmaceutical composition or kit according to the invention comprises abiraterone and enzalutamide as the at least two inhibitors of the androgen receptor pathway and LY2228820 as the p38 inhibitor.

In another most preferred embodiment, a pharmaceutical composition or kit according to the invention comprises apalutamide and abiraterone as the at least two inhibitors of the androgen receptor pathway and LY2228820 as the p38 inhibitor.

In another most preferred embodiment, a pharmaceutical composition or kit according to the invention comprises abiraterone and enzalutamide as the at least two inhibitors of the androgen receptor pathway and ARRY-614 as the p38 inhibitor.

In another most preferred embodiment, a pharmaceutical composition or kit according to the invention comprises apalutamide and enzalutamide as the at least two inhibitors of the androgen receptor pathway and ARRY-614 as the p38 inhibitor.

Alternatively, according to another particular embodiment, said combination can consist in combining a p38 inhibitor and inhibitors of the androgen receptor signaling pathway in the form of two pharmaceutical preparations. In other words, the combination can be in the form of a combination kit or product.

In such embodiment, the two pharmaceutical preparations may be administered sequentially (at different times) or concurrently (at the same time).

The pharmaceutical combination of an inhibitor of the androgen receptor signaling pathway, such as enzalutamide or abiraterone and a p38 inhibitor, such as ARRY-371797, ARRY-614 and VX-745 can in particular take the form of a kit comprising:
  (i) an inhibitor of the androgen receptor signaling pathway, such as enzalutamide or abiraterone in a first galenical formulation, and
  (ii) a p38 inhibitor, such as ARRY-371797, ARRY-614 and VX-745 in a second galenical formulation.

According to a particular embodiment, the pharmaceutical combination of an inhibitor of the androgen receptor signaling pathway, such as enzalutamide, abiraterone or apalutamide, and a p38 inhibitor, such as LY2228820 or ARRY-614 can in particular take the form of a kit comprising:
  (i) an inhibitor of the androgen receptor signaling pathway, such as enzalutamide, abiraterone or apalutamide in a first galenical formulation, and
  (ii) a p38 inhibitor, such as LY2228820 or ARRY-614 in a second galenical formulation.

According to another embodiment, the pharmaceutical composition of at least two inhibitors of the androgen receptor signaling pathway chosen among enzalutamide, abiraterone and apalutamide, and a p38 inhibitor, such as LY2228820 or ARRY-614 can in particular take the form of a kit comprising:
  (i) at least two inhibitors of the androgen receptor signaling pathway chosen among enzalutamide, abiraterone and apalutamide in a first galenical formulation, and
  (ii) a p38 inhibitor, such as LY2228820 or ARRY-614 in a second galenical formulation.

The combination can be administered repeatedly over the course of several cycles according to a protocol which depends on the nature and on the stage of the prostate cancer to be treated and also on the patient to be treated (age, weight, previous treatment(s), etc.). The protocol can be determined by any practitioner specializing in oncology.

According to a particular embodiment of the invention, radiotherapy treatments may also be administered simultaneously or sequentially.

The administration mode may be the parenteral route and/or the oral route, and is preferably the oral route.

According to a particular embodiment, the combination or composition according to the invention is in the form of an injectable or an oral composition.

According to one particular embodiment, the combination or composition can be in the form of a unit pharmaceutical preparation, in particular an oral dosage form, and more particularly a solid oral dosage form.

The doses of p38 inhibitor and of inhibitors of the androgen receptor signaling pathway administered each time to a patient depend on various parameters, such as the nature and stage of the cancer to be treated, and also on the patient to be treated (age, weight, previous treatment(s), etc.).

The pharmaceutical combination or composition of an inhibitor of the androgen receptor signaling pathway and a p38 inhibitor according to the invention can be administered repeatedly over the course of several sequences or cycles according to a protocol. The protocol can be determined by any practitioner.

All combinations of doses, frequencies and treatment period are encompassed within the scope of the present invention.

The p38 inhibitor, and in particular ARRY-371797, ARRY-614 and VX-745 can be administered daily in a range between 1 and 1500 mg, in particular between 10 and 1000 mg, and more particularly between 20 and 800 mg. The p38 inhibitor, and in particular LY2228820 and ARRY-614 can be administered daily in a range between 1 and 1500 mg, in particular between 10 and 1000 mg, and more particularly between 20 and 800 mg.

The inhibitor of the androgen receptor signaling pathway can be administered, for its part, in a range between 10 and 2000 mg per day, in particular between 20 and 1500 mg per day.

Abiraterone can be administered, for its part, in a range between 250 mg and 1000 mg per day, in particular between 500 mg and 1000 mg per day, and more particularly between 750 mg and 1000 mg per day.

For example, enzalutamide can be administered, for its part, in a range between 40 mg and 160 mg per day, in particular between 80 mg and 160 mg per day, and even more particularly between 120 mg and 160 mg per day.

For example, apalutamide can be administered, for its part, in a range between 60 mg and 240 mg per day, in particular between 120 mg and 240 mg per day, and even more particularly between 180 mg and 240 mg per day.

According to a particular embodiment, a pharmaceutical combination or a use of the invention comprises an inhibitor of the androgen receptor signaling pathway selected from abiraterone administered in a range between 250 mg and 1000 mg per day, in particular between 500 mg and 1000 mg per day, and more particularly between 750 mg and 1000 mg per day, enzalutamide administered in a range between 40 mg and 160 mg per day, in particular between 80 mg and 160 mg per day, and even more particularly between 120 mg and 160 mg per day and apalutamide administered in a range between 60 mg and 240 mg per day, in particular between 120 mg and 240 mg per day, and even more particularly between 180 mg and 240 mg per day.

When the composition according to the invention comprises at least two inhibitors of the androgen receptor signaling pathway, the at least two inhibitors of the androgen receptor signaling pathway may be administered according to the following:
  for a combination of abiraterone and enzalutamide 250 mg to 1000 mg per day for abiraterone, preferably 500 mg to 1000 mg per day and 40 mg to 160 mg per day for enzalutamide, preferably 120 mg to 160 mg per day, and
  for a combination of abiraterone and apalutamide 250 mg to 1000 mg per day for abiraterone, preferably 500 mg to 1000 mg per day and 60 mg to 240 mg per day for apalutamide, preferably 180 mg to 240 mg per day.

The present invention further relates to a pharmaceutical composition comprising enzalutamide or abiraterone and ARRY-371797, ARRY-614 and VX-745 and at least one pharmaceutically acceptable excipient. The present invention further relates to a pharmaceutical composition comprising enzalutamide, abiraterone or apalutamide and LY2228820 and ARRY-614 and at least one pharmaceutically acceptable excipient.

A medicament comprising enzalutamide or abiraterone and ARRY-371797, ARRY-614 and VX-745 is also encompassed within the scope of the present invention. A medicament comprising enzalutamide, abiraterone or apalutamide and LY2228820 and ARRY-614 is also encompassed within the scope of the present invention.

Pharmaceutical Compositions

A pharmaceutical composition according to the invention may comprise at least one pharmaceutically acceptable excipient.

A pharmaceutically acceptable carrier or excipient refers to a non-toxic solid, semi-solid or liquid filler, diluent, encapsulating material or formulation auxiliary of any type. In the pharmaceutical compositions of the invention for oral, sublingual, subcutaneous, intramuscular, intravenous, transdermal, the active principle, alone or in combination with another active principle, can be administered in a unit administration form, as a mixture with conventional pharmaceutical supports, to animals and human beings.

Suitable unit administration forms comprise oral-route forms such as tablets, gel capsules, powders, granules and oral suspensions or solutions, sublingual and buccal administration forms, aerosols, implants, subcutaneous, transdermal, intraperitoneal, intramuscular, intravenous, subdermal, transdermal, and intrathecal administration forms.

According to a particular embodiment, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions. The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. Solutions comprising compounds of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms. The peptide or the drug conjugate (or the vector comprising peptide or the drug conjugate) can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin. Sterile injectable solutions are prepared by incorporating the active polypeptides in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1,000 ml of hypodermoclysis fluid or injected at the proposed site of infusion. Some variation in dosage will necessarily occur depending on the condition of the subject being treated.

According to a particular embodiment, a pharmaceutical composition according to the invention comprises from 60 mg to 240 mg, preferably from 180 mg to 240 mg of apalutamide, from 250 mg to 1000 mg, preferably from 500 mg to 1000 mg of abiraterone and/or from 40 mg to 160 mg, preferably, from 120 mg to 160 mg of enzalutamide.

According to a particular embodiment, a pharmaceutical composition according to the invention comprises from 10 mg to 560 mg, preferably from 300 mg to 560 mg of LY2228820 and/or from 100 mg to 1200 mg, preferably from 900 mg to 1200 mg of ARRY-614.

According to a particular embodiment, when the inhibitor of the androgen receptor signaling pathway is enzalutamide and the p38 inhibitor is LY2228820, LY2228820 is present in the composition in an amount ranging from 10 mg to 560 mg, preferably from 300 mg to 560 mg, and the enzalutamide is present in an amount ranging from 40 mg to 160 mg, preferably from 120 mg to 160 mg.

According to another particular embodiment, when the inhibitor of the androgen receptor signaling pathway is enzalutamide and the p38 inhibitor is ARRY-614, ARRY-614 is present in the composition in an amount ranging from 100 mg to 1200 mg, preferably from 900 mg to 1200 mg, and the enzalutamide is present in an amount ranging from 40 mg to 160 mg, preferably from 120 mg to 160 mg.

According to a particular embodiment, when the inhibitor of the androgen receptor signaling pathway is abiraterone and the p38 inhibitor is LY2228820, LY2228820 is present in the composition in an amount ranging from 10 mg to 560 mg, preferably from 300 mg to 560 mg, and the abiraterone is present in an amount ranging from 250 mg to 1000 mg, preferably from 500 mg to 1000 mg.

According to a particular embodiment, when the inhibitor of the androgen receptor signaling pathway is abiraterone and the p38 inhibitor is ARRY-614, ARRY-614 is present in the composition in an amount ranging from 100 mg to 1200 mg, preferably from 900 mg to 1200 mg, and the abiraterone is present in an amount ranging from 250 mg to 1000 mg preferably from 500 mg to 1000 mg.

According to a particular embodiment, when the inhibitor of the androgen receptor signaling pathway is apalutamide and the p38 inhibitor is LY2228820, LY2228820 is present in the composition in an amount ranging from 10 mg to 560 mg, preferably from 300 mg to 560 mg, and the apalutamide is present in an amount ranging from 60 mg to 240 mg, preferably from 180 mg to 240 mg.

According to a particular embodiment, when the inhibitor of the androgen receptor signaling pathway is apalutamide and the p38 inhibitor is ARRY-614, ARRY-614 is present in the composition in an amount ranging from 100 mg to 1200 mg, preferably from 900 mg to 1200 mg, and the apalutamide is present in an amount ranging from 60 mg to 240 mg, preferably from 180 mg to 240 mg.

According to another embodiment, when the inhibitors of the androgen receptor signaling pathway are apalutamide and abiraterone and the p38 inhibitor is LY2228820, apalutamide is present in the composition in an amount ranging from 60 mg to 240 mg, preferably from 180 mg to 240 mg, abiraterone is present in an amount ranging from 250 mg to 1000 mg preferably from 500 mg to 1000 mg, and LY2228820 is present in an amount ranging from 10 mg to 560 mg, preferably from 300 mg to 560 mg.

According to another embodiment, when the inhibitors of the androgen receptor signaling pathway are apalutamide and abiraterone and the p38 inhibitor is ARRY-614, apalutamide is present in the composition in an amount ranging from 60 mg to 240 mg, preferably from 180 mg to 240 mg, abiraterone is present in an amount ranging from 250 mg to 1000 mg preferably from 500 mg to 1000 mg, and ARRY-614 is present in an amount ranging from 100 mg to 1200 mg, preferably from 900 mg to 1200 mg.

According to another embodiment, when the inhibitors of the androgen receptor signaling pathway are enzalutamide and abiraterone and the p38 inhibitor is LY2228820, enzalutamide is present in the composition in an amount ranging from 40 mg to 160 mg, preferably from 120 mg to 160 mg, abiraterone is present in an amount ranging from 250 mg to 1000 mg preferably from 500 mg to 1000 mg, and LY2228820 is present in an amount ranging from 10 mg to 560 mg, preferably from 300 mg to 560 mg.

According to another embodiment, when the inhibitors of the androgen receptor signaling pathway are enzalutamide and abiraterone and the p38 inhibitor is ARRY-614, enzalutamide is present in the composition in an amount ranging from 40 mg to 160 mg, preferably from 120 mg to 160 mg, abiraterone is present in an amount ranging from 250 mg to 1000 mg preferably from 500 mg to 1000 mg, and ARRY-614 is present in an amount ranging from 100 mg to 1200 mg, preferably from 900 mg to 1200 mg.

According to a particular embodiment, the pharmaceutical combination or composition according to the present invention may be co-administered with radiotherapy or at least another antitumor agent, in particular active against prostate cancer. Among such antitumor agents docetaxel, cabazitaxel, estramustine and diethylstilbestrol may be cited.

The pharmaceutical combination or composition according to the present invention may also be co-administered with at least another active ingredient that may be beneficial to the global treatment of the patient.

As a way of example, prednisone can advantageously be co-administered to a patient treated with abiraterone. Indeed, the inhibition of androgen synthesis induced by abiraterone may provoke a secondary hyperaldosreronism.

The present invention further encompasses a method for therapeutic treatment of prostate cancer, and in particular for therapeutic treatment of castration-resistant prostate cancer, consisting in administering to patients, in need thereof, an effective amount of enzalutamide or abiraterone and an effective amount of a p38 inhibitor, in particular 2ARRY-371797, ARRY-614 and VX-745, it being possible for their administration to be carried out separately, simultaneously or spread out over time.

The present invention further encompasses a method for therapeutic treatment of prostate cancer, and in particular for therapeutic treatment of castration-resistant prostate cancer, consisting in administering to patients, in need thereof, an effective amount of enzalutamide, abiraterone or apalutamide and an effective amount of a p38 inhibitor, in particular LY2228820 and ARRY-614, it being possible for their administration to be carried out separately, simultaneously or spread out over time.

The present invention further encompasses a method for therapeutic treatment of prostate cancer, and in particular for therapeutic treatment of castration-resistant prostate cancer, consisting in administering to patients, in need thereof, an effective amount of at least two of enzalutamide, abiraterone and apalutamide and an effective amount of a p38 inhibitor, in particular LY2228820 and ARRY-614, it being possible for their administration to be carried out separately, simultaneously or spread out over time.

The present invention further encompasses a method for therapeutic treatment of prostate cancer, and in particular for therapeutic treatment of castration-resistant prostate cancer, consisting in administering to patients, in need thereof, an effective amount of at least one of enzalutamide or apalutamide, an effective amount of abiraterone and an effective amount of a p38 inhibitor, in particular LY2228820 and ARRY-614, it being possible for their administration to be carried out separately, simultaneously or spread out over time.

The present application also relates to a method for therapeutic treatment of prostate cancer, and in particular for therapeutic treatment of castration-resistant prostate cancer, consisting in administering to patients suffering of a prostate cancer associated with AR-V7 variant androgen receptor protein expressing cells, in need thereof, an effective amount of at least an inhibitor of the androgen receptor signaling pathway and an effective amount of a p38 inhibitor, it being possible for their administration to be carried out separately, simultaneously or spread out over time.

The present application also relates to a method for therapeutic treatment of prostate cancer, and in particular for therapeutic treatment of castration-resistant prostate cancer, consisting in administering to patients suffering of a prostate cancer associated with AR-V7 variant androgen receptor protein expressing cells, in need thereof, an effective amount of at least two inhibitors of the androgen receptor signaling pathway and an effective amount of a p38 inhibitor, it being possible for their administration to be carried out separately, simultaneously or spread out over time.

The present application also relates to a method for therapeutic treatment of prostate cancer, and in particular for therapeutic treatment of castration-resistant prostate cancer, consisting in administering to patients suffering of a prostate cancer associated with AR-V7 variant androgen receptor protein expressing cells, in need thereof, an effective amount of at least one of enzalutamide or apalutamide, an effective amount of abiraterone and an effective amount of a p38 inhibitor, it being possible for their administration to be carried out separately, simultaneously or spread out over time.

In other words, the said prostate tumour cells express the androgen receptor variant AR-V7.

The present application also relates to a method for preventing the occurrence of resistance for patients suffering from prostate cancer treated by at least an inhibitor of the androgen receptor signaling pathway consisting in administering to patients suffering of a prostate cancer in need thereof, an effective amount of at least an inhibitor of the androgen receptor signaling pathway and an effective amount of a p38 inhibitor, it being possible for their administration to be carried out separately, simultaneously or spread out over time.

The present application also relates to a method for preventing the occurrence of resistance for patients suffering from prostate cancer treated by at least an inhibitor of the androgen receptor signaling pathway consisting in administering to patients suffering of a prostate cancer in need thereof, an effective amount of at least two inhibitors of the androgen receptor signaling pathway and an effective amount of a p38 inhibitor, it being possible for their administration to be carried out separately, simultaneously or spread out over time.

The present application also relates to a method for preventing the occurrence of resistance for patients suffering from prostate cancer treated by an inhibitor of the androgen receptor signaling pathway consisting in administering to patients suffering of a prostate cancer in need thereof, an effective amount of at least one of enzalutamide or apalutamide, an effective amount of abiraterone and an effective amount of a p38 inhibitor, it being possible for their administration to be carried out separately, simultaneously or spread out over time.

According to a particular embodiment, the present invention provides a method for treating prostate cancer in a subject comprising administering to the subject a p38 inhibitor and at least an inhibitor of the androgen receptor signaling pathway, in an amount effective to treat, wherein the subject is identified as having prostate cancer cells expressing the androgen receptor protein with an elevated level of AR-V7 variant relative to a reference level.

According to a particular embodiment, the present invention provides a method for treating prostate cancer in a subject comprising administering to the subject a p38 inhibitor and at least two inhibitors of the androgen receptor signaling pathway, in an amount effective to treat, wherein the subject is identified as having prostate cancer cells expressing the androgen receptor protein with an elevated level of AR-V7 variant relative to a reference level.

According to a particular embodiment, the present invention provides a method for treating prostate cancer in a subject comprising administering to the subject a p38 inhibitor, at least one of enzalutamide or apalutamide, and abiraterone, in an amount effective to treat, wherein the subject is identified as having prostate cancer cells expressing the androgen receptor protein with an elevated level of AR-V7 variant relative to a reference level.

The present invention is illustrated by, without being limited to, the examples hereafter.

EXAMPLES

Example 1: Abiraterone and Enzalutamide Activate MAPK p38

The inventors have tested in the present example if both drugs, abiraterone or enzalutamide could activate the stress kinase p38 (MAPK14). Prostate cancer cell lines 22Rv1 (Androgen Receptor expressing cells and AR-V7) and LNCaP (Androgen Receptor expressing cells) cells have been treated with abiraterone (FIG. 1) and with enzalutamide (FIG. 2) and the activation of p38 was tested by using a specific antibody targeting the phosphorylated form of p38, which is a readout for its activation These experiments show, for the first time, that abiraterone and enzalutamide activates the MAPK p38 in prostate cancer cells.

Example 2: In Vitro Synergistic Effect of the Combination of Abiraterone or Enzalutamide and p38 Inhibitor Said example is aimed at proving that the combination of the p38 inhibitor SB202190 can enhance the abiraterone or enzalutamide effect on androgenic receptor expressing prostate cancer cells.

A cytotoxic assay was performed using the sulforhodamine B staining to address the cell viability and using:
  6 different concentrations of SB202190 (1.25, 2.5, 5, 10 20 and 40 µM) and 5 different concentrations of abiraterone (1.87, 3.75, 7.5, 15 and 30 µM) consisting in 30 different drug combinations (FIG. 3).
  5 concentrations of enzalutamide (3.12, 6.25, 12.5, 25 and 50 µM) versus 4 concentrations of SB202190 (2.5, 5, 10 and 20 µM) consisting in 20 different drug combinations (FIG. 4).

The detection of synergy was addressed by mean of dose matrices, according to a modified version of the method proposed by Lehár (Lehár, J., Krueger, A. S., Avery, W., Heilbut, A. M., Johansen, L. M., Price, E. R., Rickles, R. J., Short, G. F., Staunton, J. E., Jin, X., et al. (2009). Synergistic drug combinations tend to improve therapeutically relevant selectivity. Nat. Biotechnol. 27, 659-666.) and using the equations of Loewe and Bliss for estimation of additivity. Using the Lehar method it is possible to obtain a point-by-point estimation. The results of the viability and synergism were represented screening in two matrices with shades of grey codes corresponding to the value of viability (Matrix A) and value of synergism (Matrix B, black for antagonism and additivity, grey for synergism). The combination was tested on two cells lines displaying androgen receptor (LNCaP and 22Rv1).

Figure 3B:
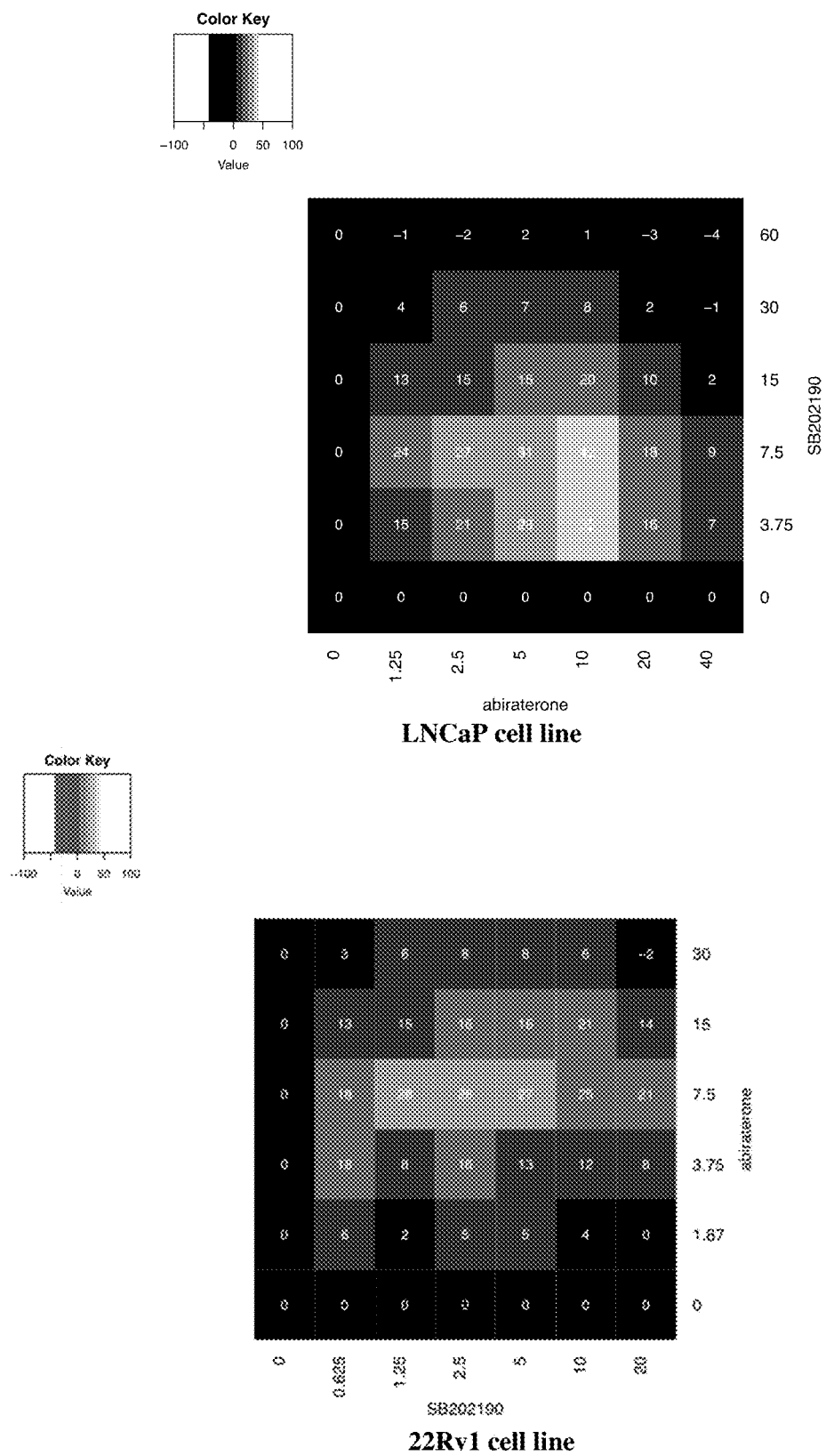
FIG. 3: In vitro double combination study and synergism 2D-analysis for the combination of abiraterone and the p38 inhibitor SB202190. Experimental survival data (A) and synergism (B) matrices for different prostate cancer cell lines LNCaP and 22Rv1 (3A and 3B) incubated with the combination at the indicated concentrations. In the experimental data matrices, values indicate the percentage of surviving cells. In the synergism matrices, the "shades of grey" scale is used to indicate antagonist or additive combinations (black) and synergistic combinations (gray, with lighter gray corresponding to more intense synergism) (Example 2).

The in vitro experiments show that the combination of abiraterone and SB202190 (p38 inhibitor) is highly synergistic in the two cell lines tested (LNCaP and 22Rv1), expressing Androgenic Receptor (FIG. 3). It was in other words observed that the synergistic effect is well pronounced in Androgen Receptor positive cell lines.

FIG. 4 shows that the combination of enzalutamide and SB202190 is highly synergistic in Androgen Receptor positive cell lines (LNCaP and 22Rv1).

Example 3: p38 Inhibitor Combined with Abiraterone or Enzalutamide is Synergistic In Vivo An in vivo experiment was performed in preclinical prostate cancer model, to confirm the synergistic effect as demonstrated in example 2. The LNCaP cells were used, as they show a p38 activation upon abiraterone or enzalutamide induction, and a high synergistic effect.

The combination of abiraterone+p38 inhibitor (SB202190) and enzalutamide+p38 inhibitor (SB202190) in vivo was tested.

Figure 5:
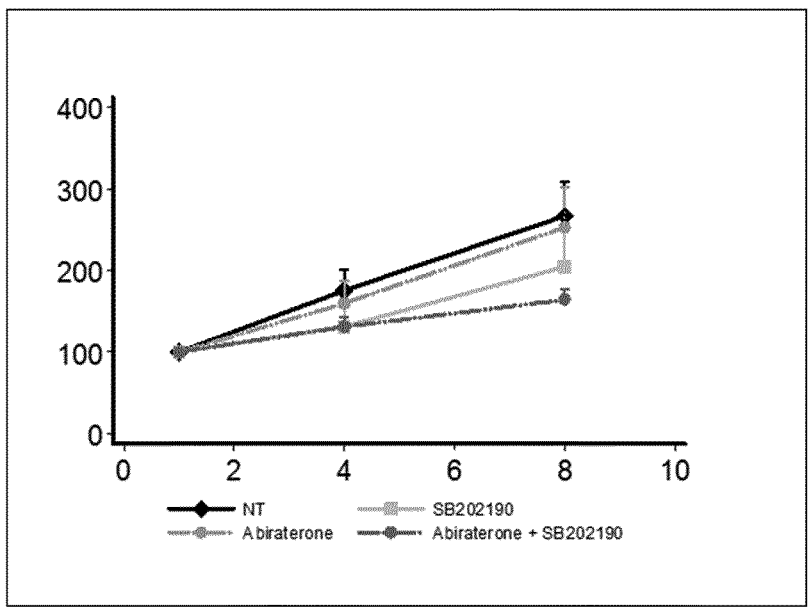
FIG. 5: Abiraterone and SB202190 are synergistic in vivo. NOD/SCID male mice have been xenografted with LNCaP cells subcutaneously and when the tumor reached 100 mm$^3$, the mice were treated (Example 3).

The human prostate cancer cell line LNCaP was xenografted in 24 NOD/SCID male mice for each combination (3 $10^6$ cells per mice in matrigel, subcutaneously) and the mice were treated when the tumor reach 100 mm$^3$. The mice were divided into four groups:
  Non-Treated, abiraterone (50 mg/kg, day1 and 12.5 mg/kg day 3 gavage), SB202190 (0.05 µmol/kg/day, I.P.), and abiraterone+SB202190 (FIG. 5).
  Non-Treated, enzalutamide (25 mg/kg/day, gavage), SB202190 (0.05 µmol/kg/day, I.P.), and enzalutamide+SB202190 (FIG. 6).

FIG. 5 shows that the combination (abiraterone+SB202190) displays a major anti-tumor effect compared to the control mice and even compared to the single drug treatments (abiraterone alone or SB202190 alone).

Figure 6:
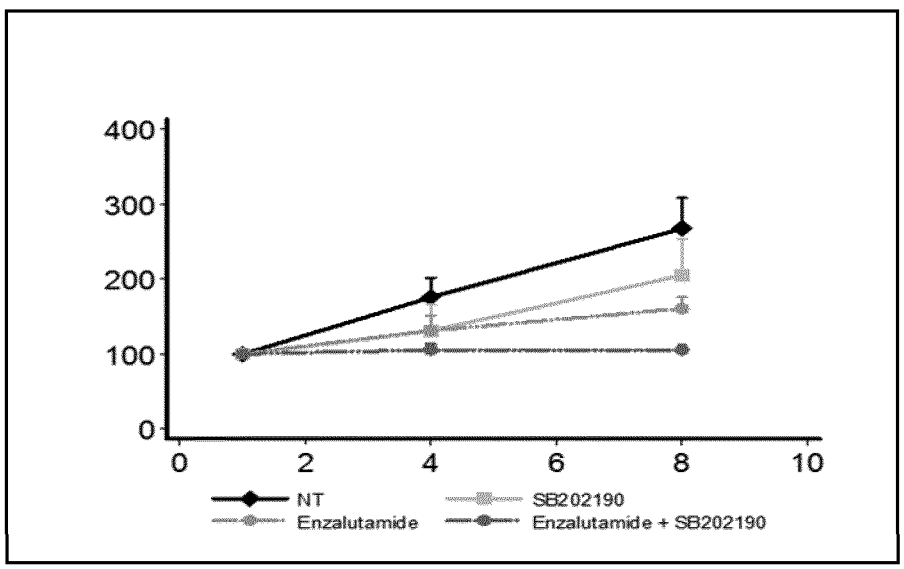
FIG. 6: Enzalutamide and SB202190 are synergistic in vivo. NOD/SCID male mice have been xenografted with LNCaP cells subcutaneously and when the tumor reached 100 mm$^3$, the mice were treated (Example 3).

FIG. 6 shows that the combination (enzalutamide+SB202190) displays a major anti-tumor effect compared to the control mice and even compared to the single drug treatments (enzalutamide alone or SB202190 alone).

Example 4: Identification of Target of the p38 Inhibitor

Figure 7:
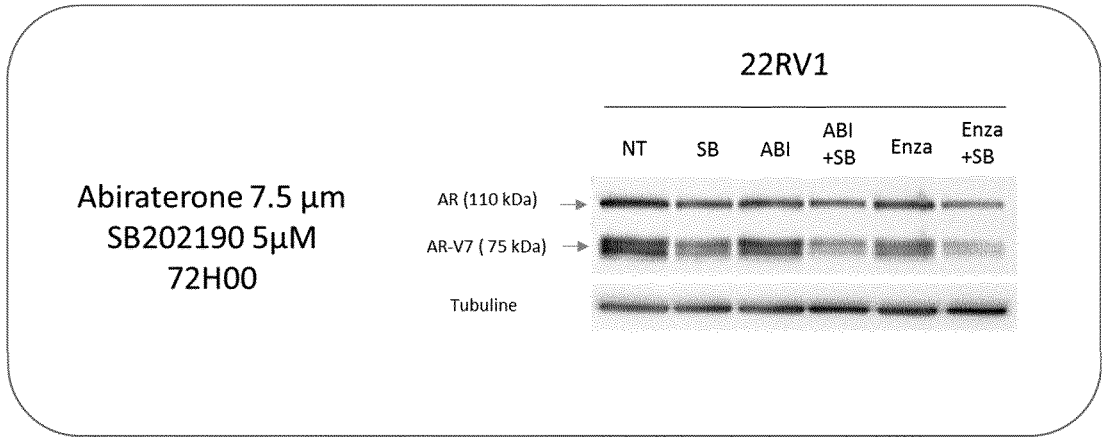
FIG. 7: The p38 inhibitor SB202190 inhibits AR-V7 expression in 22Rv1 prostate cancer cell line. Prostate cancer cells 22Rv1 were treated with abiraterone (7.5 µM), enzalutamide (7.5 µM), SB202190 (504), abiraterone+SB202190 or enzalutamide+SB202190 during 72 hours. Proteins were extracted and subjected to western blot analysis using anti-AR, anti-AR-V7 and anti-tubulin antibodies (Example 4).
Figure 12:
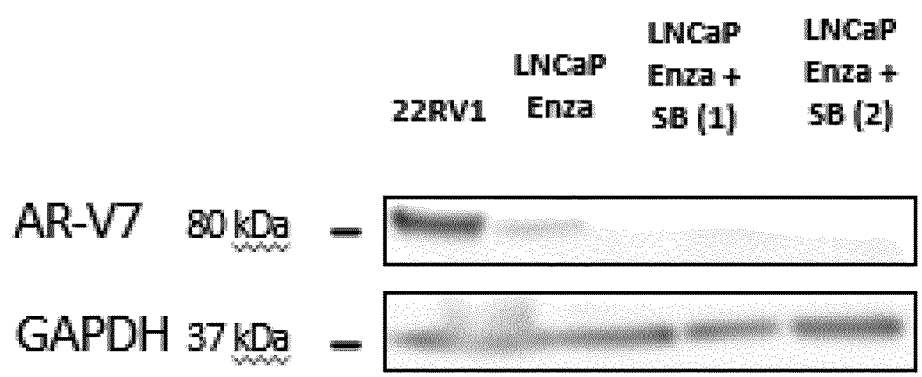
FIG. 12: Long term culture of LNCaP with enzalutamide induces AR-V7 expression that is reduced when cell culture is co-treated with the p38 inhibitor SB202190. LNCaP prostate cancer cells (AR-V7 negative) were treated with 30 µM enzalutamide during 45 days +/−5 µM of the p38 inhibitor SB202190. Protein were extracted and subjected to Western blot analysis using anti-ARV7 and anti-GAPDH (to serve as a loading control) antibodies (example 9).

Western blot analysis was performed, detecting the wild-type form of AR and the AR-V7 form as well (FIG. 7). In this way the inventors tested the involvement of the p38 inhibitor in abiraterone and enzalutamide resistance, the AR-V7.

It has thus been observed that the combination of the p38 inhibitor with abiraterone or enzalutamide lead to a marked inhibition of AR-V7 expression.

Example 5: In Vitro Synergistic Effect of the Combination of Enzalutamide and a p38 Inhibitor Said example is aimed at proving that the combination of the p38 inhibitors LY2228820 and ARRY-614 can enhance the enzalutamide effect on androgenic receptor expressing prostate cancer cells.

A cytotoxic assay was performed using the sulforhodamine B staining to address the cell viability and using 5 different concentrations of LY2228820 or ARRY-614 (1.125, 2.5, 5, 10 and 20 µM) and 7 different concentrations of enzalutamide (0.625, 1.25, 2.5, 5, 10, 20 and 40 µM) consisting in 35 different drug combinations (FIG. 8).

The detection of synergy was addressed by mean of dose matrices, as in example 2 above. The results of the viability and synergism were represented screening in two matrices with shades of grey codes corresponding to the value of viability (above) and value of synergism (below) (black for antagonism and additivity, grey for synergism). The combination was tested on 22Rv1 cells.

The in vitro experiments show that the combination of enzalutamide and LY2228820 or ARRY-614 (p38 inhibitors) shows synergism in 22Rv1 cells, expressing Androgenic Receptor (FIG. 8). It was in other words observed that the synergistic effect is well pronounced on AR-V7 expressing cell lines.

Example 6: In Vitro in Spheroid Cell Culture Synergistic Effect of the Combination of Ezalutamide, Abiraterone or Apalutamide and a p38 Inhibitor Said example is aimed at proving that the combination of p38 inhibitors LY2228820 and ARRY-614 can enhance the enzalutamide, abiraterone or apalutamide effect on androgenic receptor expressing prostate cancer cells.

A cytotoxic 3D culture assay was performed using the cell titer glo staining to address the cell viability and using different concentrations of LY2228820 or ARRY-614 and different concentrations of enzalutamide, abiraterone or apalutamide (FIG. 9).

3D cell culture is closer to tumor growth and response to drug than 2D culture on plastic plate that is far from physiological conditions. This 3D cell culture allows close interaction between cells and spheroid culture mimic the hypoxia and nutriment gradient observed in vivo. Cell titer glow and measure of spheroid volume allow a precise quantification of the drug effect.

The in vitro experiments show that the combination of any one of enzalutamide, abiraterone or apalutamide and LY2228820 or ARRY-614 (p38 inhibitors) shows synergism in the 22Rv1 cells, expressing Androgenic Receptor (FIG. 9). It was in other words observed that the synergistic effect is well pronounced in AR-V7 expressing cell lines.

Example 7: In Vitro Synergistic Effect of the Combination of Two Inhibitors of the Androgen Receptor Signaling Pathway (i.e. Enzalutamide and Abiraterone) and a p38 Inhibitor (LY2228820 or ARRY-614)—Triple Combination Said example is aimed at proving that the combination of a p38 inhibitor with at least two inhibitors of the androgen receptor signaling pathway can enhance their effect on androgenic receptor expressing prostate cancer cells.

A cytotoxic assay was performed using the CELL TITER GLOW staining to address the cell viability and using different concentrations of enzalutamide and abiraterone in the absence or in the presence of increasing concentrations of LY2228820 (FIG. 10) and ARRY-614 (FIG. 11).

The detection of synergy was addressed by mean of dose matrices, as in example 2 above. The results of the viability and synergism were represented screening in two matrices with shades of grey codes corresponding to the value of viability (above) and value of synergism (below) (black for antagonism and additivity, grey for synergism). The combination was tested on 22Rv1 cells.

The in vitro experiments show that the triple combination of at least two inhibitors of the androgen receptor signaling pathway such as enzalutamide and abiraterone with a p38 inhibitor such as LY2228820 or AARY-614 shows synergism in the 22Rv1 cell line (FIGS. 10 and 11).

Example 8: Microscope Observation of AR-V7 Expression in 22Rv1 Cells

The expression of AR-V7 was observed by the CELIGO microscope in 22Rv1 cells after 72 hours of culture. A first group of cells, the control group, was observed in the absence of any inhibitor. Five other cell groups were observed in the presence of SB202190 5 µM, in the presence of enzalutamide 30 µM, in the presence of LY2228820 2.5 µM, in the presence of enzalutamide 30.0 µM and SB202190 5.0 µM and in the presence of enzalutamide 30.0 µM and LY2228820 2.5 µM.

After 72 hours, the following results were observed:

| Inhibitors added | % of cells with ARv7 |
| --- | --- |
| None (control) | 30.0% |
| Enzalutamide 30.0 µM | 31.0% |
| SB202190 5.0 µM | 28.0% |
| LY2228820 2.5 µM | 34.0% |
| Enzalutamide 30.0 µM + SB202190 5.0 µM | 15.0% |
| Enzalutamide 30.0 µM + LY2228820 2.5 µM | 6.0% |

These results clearly demonstrate that the in vitro administration of a combination of an inhibitor of the androgen receptor signaling pathway and a p38 inhibitor reduced the expression of the AR-V7 variant in Androgen Receptor expressing cells. This result confirms the western blot shown in FIG. 7.

Example 9: Appearance of Resistance on LNCaP Cells

LNCaP cells are cultivated for 45 days:
(i) with enzalutamide 30.0 µM, and
(ii) with enzalutamide 30.0 µM and SB202190 5.0 µM (this culture was duplicated as illustrated by SB(1) and SB(2) of FIG. 12).

Western blot analysis was performed to detect the AR-V7 form (FIG. 12) in the cells. GADPH represents the loading control.

In this way the inventors tested the induction of AR-V7 expression induced by long-term treatment with enzalutamide in LNCaP cells (cells that are normally AR-V7 negative) in the presence of enzalutamide (second well).

It has been noticed that in the additional presence of the p38 inhibitor the expression of AR-V7 is clearly reduced (third and fourth wells).

It has thus been observed that the combination of the p38 inhibitor with enzalutamide prevents the occurrence of AR-V7 expression and then the occurrence of a resistance.

The invention claimed is:

1. Method for treating prostate cancer in individuals wherein the prostate tumor cells express the AR-V7 variant androgen receptor protein, or for preventing the occurrence of resistance in patients suffering from prostate cancer treated by an inhibitor of the androgen receptor signaling pathway, comprising administering to said individuals a pharmaceutical combination of an inhibitor of the androgen receptor signaling pathway and a p38 inhibitor, wherein the p38 inhibitor is selected from the group consisting of LY2228820 and ARRY-614 and wherein the inhibitor of the androgen receptor signaling pathway is selected from enzalutamide, apalutamide, bicalutamide, nilutamide, flutamide, abiraterone, ketoconazole, darolutamide, and orteronel.

2. Method according to claim 1, wherein the p38 inhibitor is administered in a daily dosage ranging between 1 and 1500 mg.

3. Method according to claim 1, wherein the inhibitor of the androgen receptor signaling pathway is administered in a range between 10 and 2000 mg per day.

4. Method according to claim 3, wherein the inhibitor of the androgen receptor signaling pathway is selected from abiraterone administered in a range between 250 mg and 1000 mg per day, enzalutamide administered in a range between 40 mg and 160 mg per day, and apalutamide administered in a range between 60 mg and 240 mg per day.

5. Method according to claim 1, wherein the p38 inhibitor and the inhibitor of the androgen receptor signaling pathway are used simultaneously, separately or are spread out over time.

6. A pharmaceutical composition comprising enzalutamide, abiraterone or apalutamide and a p38 inhibitor selected from LY2228820 and ARRY-614, and at least one pharmaceutically acceptable excipient.

7. Method for restoring the sensitivity to androgen-deprivation therapy (ADT) in patients suffering from prostate cancers having acquired a resistance to ADT following a treatment with an inhibitor of the androgen receptor signaling pathway and wherein the prostate tumour cells express the AR V7 variant androgen receptor protein, comprising administering to said patients a p38 inhibitor, wherein the p38 inhibitor is selected from the group consisting of LY2228820 and AARY-614 and wherein the inhibitor of the androgen receptor signaling pathway is selected from enzalutamide, apalutamide, bicalutamide, nilutamide, flutamide, abiraterone, ketokonazole, darolutamide, and orteronel.

8. A pharmaceutical composition comprising at least two inhibitors of the androgen receptor signaling pathway and at least one p38 inhibitor selected from LY2228820 and ARRY-614.

9. Pharmaceutical composition according to claim 8, wherein the at least two inhibitors of the androgen receptor signaling pathway are selected from enzalutamide, apalutamide, bicalutamide, nilutamide, flutamide, abiraterone, ketokonazole, darolutamide and orteronel.

10. Pharmaceutical composition according to claim 8, wherein the composition comprises from 60 mg to 240 mg of apalutamide, from 250 mg to 1000 mg of abiraterone and/or from 40 mg to 160 mg of enzalutamide.

11. Pharmaceutical composition according to claim 8, wherein the composition comprises from 10 mg to 560 mg of LY2228820 and/or from 100 mg to 1200 mg of ARRY-614.

12. Pharmaceutical composition according to claim 8, wherein the p38 inhibitor and the at least two inhibitors of the androgen receptor signaling pathway are used simultaneously, separately or are spread out over time.

13. Pharmaceutical composition according to claim 8, wherein the composition is in the form of an injectable or an oral composition.

14. Method for treating prostate cancer in individuals wherein the prostate tumor cells express the AR-V7 variant androgen receptor protein, or for preventing the occurrence of resistance in patients suffering from prostate cancer treated by an inhibitor of the androgen receptor signaling pathway, comprising administering a pharmaceutical composition according to claim 8 to said individuals.

* * * * *